US008535888B2

(12) United States Patent
Aichinger et al.

(10) Patent No.: US 8,535,888 B2
(45) Date of Patent: Sep. 17, 2013

(54) COMPOSITIONS AND METHODS FOR DETECTING METHICILLIN-RESISTANT *S. AUREUS*

(75) Inventors: Christian Aichinger, Munich (DE); Astrid Reiser, Antdorf (DE); James R. Uhl, Rochester, MN (US); Franklin R. Cockerill, III, Rochester, MN (US)

(73) Assignees: Mayo Foundation for Medical Education and Research, Rochester, MN (US); Roche Molecular Systems, Pleasanton, CA (US)

( * ) Notice: Subject to any disclaimer, the term of this patent is extended or adjusted under 35 U.S.C. 154(b) by 863 days.

(21) Appl. No.: 11/966,287

(22) Filed: Dec. 28, 2007

(65) Prior Publication Data

US 2008/0220428 A1 Sep. 11, 2008

Related U.S. Application Data

(60) Provisional application No. 60/882,799, filed on Dec. 29, 2006.

(51) Int. Cl.
*C12Q 1/68* (2006.01)
*C12P 19/34* (2006.01)
*C12N 9/00* (2006.01)
*C07H 21/04* (2006.01)

(52) U.S. Cl.
USPC ......... 435/6.12; 435/91.2; 435/183; 536/24.3

(58) Field of Classification Search
None
See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,800,159 | A | 1/1989 | Mullis et al. |
| 4,965,188 | A | 10/1990 | Mullis et al. |
| 4,996,143 | A | 2/1991 | Heller et al. |
| 5,035,996 | A | 7/1991 | Hartley |
| 5,386,024 | A | 1/1995 | Kacian et al. |
| 5,565,322 | A | 10/1996 | Heller |
| 5,683,896 | A | 11/1997 | Hartley et al. |
| 5,849,489 | A | 12/1998 | Heller |
| 5,945,313 | A | 8/1999 | Hartley et al. |
| 6,156,507 | A | 12/2000 | Hiramatsu et al. |
| 6,162,603 | A | 12/2000 | Heller |
| 6,174,670 | B1 | 1/2001 | Wittwer et al. |
| 6,593,093 | B1 | 7/2003 | Uhl et al. |
| 6,830,888 | B2 | 12/2004 | Cockerill et al. |
| 6,849,407 | B2 | 2/2005 | Espy et al. |
| 6,958,210 | B2 | 10/2005 | Smith et al. |
| 7,074,598 | B2 | 7/2006 | Cockerill, III et al. |
| 7,074,599 | B2 | 7/2006 | Uhl et al. |
| 7,365,176 | B2 | 4/2008 | Smith et al. |
| 7,427,475 | B2 | 9/2008 | Uhl et al. |
| 7,452,984 | B2 | 11/2008 | Espy et al. |
| 7,615,352 | B2 | 11/2009 | Smith et al. |
| 7,667,025 | B2 | 2/2010 | Smith et al. |
| 7,691,571 | B2 | 4/2010 | Cockerill, III et al. |
| 7,790,875 | B2 | 9/2010 | Uhl et al. |
| 2003/0082563 | A1 | 5/2003 | Bell et al. |
| 2003/0165866 | A1 | 9/2003 | Cockerill et al. |
| 2003/0215814 | A1 | 11/2003 | Cockerill, III et al. |
| 2004/0014118 | A1 | 1/2004 | Uhl et al. |
| 2004/0029105 | A1 | 2/2004 | Smith et al. |
| 2005/0019893 | A1* | 1/2005 | Huletsky et al. ............ 435/252.3 |
| 2005/0282194 | A1 | 12/2005 | Cockerill, III et al. |
| 2006/0099596 | A1* | 5/2006 | Haberhausen et al. ............ 435/6 |
| 2006/0199200 | A1 | 9/2006 | Uhl et al. |
| 2007/0031866 | A1 | 2/2007 | Cockerill, III et al. |
| 2007/0054296 | A1 | 3/2007 | Piepenburg et al. |
| 2007/0082340 | A1* | 4/2007 | Huletsky et al. .................. 435/6 |
| 2007/0238093 | A1 | 10/2007 | Espy et al. |
| 2007/0238095 | A1 | 10/2007 | Espy et al. |
| 2008/0220428 | A1 | 9/2008 | Aichinger et al. |
| 2009/0171245 | A1 | 7/2009 | Uhl et al. |
| 2009/0203021 | A1 | 8/2009 | Cockerill, III et al. |
| 2010/0184018 | A1 | 7/2010 | Smith et al. |
| 2010/0221715 | A1 | 9/2010 | Cockerill, III et al. |
| 2010/0227322 | A1 | 9/2010 | Cockerill, III et al. |
| 2010/0291582 | A1 | 11/2010 | Uhl et al. |

FOREIGN PATENT DOCUMENTS

| DE | 37 34 442 | 4/1989 |
| EP | 1 529 847 | 4/2006 |
| WO | WO 91/12079 | 8/1991 |
| WO | WO 96/41811 | 12/1996 |
| WO | WO 97/46707 | 12/1997 |
| WO | WO 97/46712 | 12/1997 |
| WO | WO 97/46714 | 12/1997 |
| WO | WO 98/04730 | 2/1998 |
| WO | WO 99/16781 | 4/1999 |

(Continued)

OTHER PUBLICATIONS

Lowe et al. A computer program for selection of oligonucleotide primers for polymerase chain reactions. Nucleic Acids Res. (1990) vol. 18, No. 7, pp. 1757-1761.*
Elsayed et al. Development and validation of a molecular beacon-probe real-time polymerase chain reaction assay for rapid detection of methicillin resistance in *Staphylococcus aureus*. Arch. Patho. Lab. Med. (2003) vol. 127, pp. 845-849.*
GenBank Accession No. AB033763, dated Oct. 27, 2006, 21 pgs.
GenBank Accession No. D86934, dated Oct. 28, 2006, 27 pgs.
GenBank Accession No. AB047089, dated Nov. 2, 2006, 15 pgs.
GenBank Accession No. AB063172, dated Oct. 27, 2006, 13 pgs.
GenBank Accession No. AB121219, dated Oct. 26, 2006, 14 pgs.
Alderton et al., "Magnetic Bead Purification of M13 DNA Sequencing Templates," *Anal. Biochem.*, 1992, 201:166-169.
Cuny and Witte, "PCR for the identification of methicillin-resistant *Staphylococcus aureus* (MRSA) strains using a single primer pair specific for SCC*mec* elements and the neighbouring chromosome-borne *orfX*," *Clin. Microbiol. Infect.*, 2005, 11(10):834-837.

(Continued)

*Primary Examiner* — Kenneth R. Horlick
*Assistant Examiner* — David Thomas
(74) *Attorney, Agent, or Firm* — Fish & Richardson P.C.

(57) ABSTRACT

The present invention relates to methods of detecting the presence or absence of methicillin-resistant *S. aureus* (MRSA) in a sample, the method comprising performing an amplifying step, a hybridizing step and a detecting step. Furthermore, the present invention relates to primers, probes and kits for the detection of MRSA.

37 Claims, 5 Drawing Sheets

(56) References Cited

FOREIGN PATENT DOCUMENTS

Figure 4A:
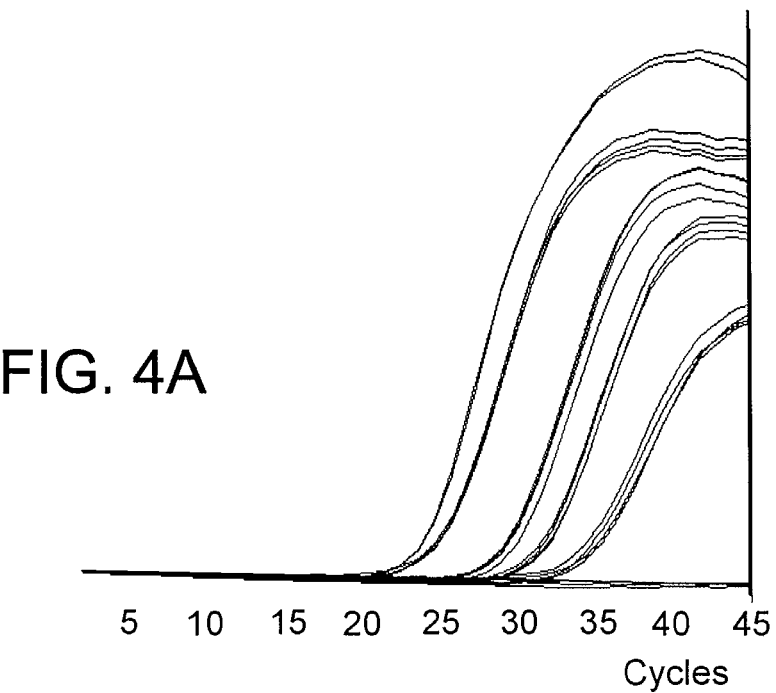

| WO | WO 01/37291 | 5/2001 |
|---|---|---|
| WO | WO 02/12263 | 2/2002 |
| WO | WO 02/099034 | 12/2002 |
| WO | WO 2006/111028 | 10/2006 |

OTHER PUBLICATIONS

Enright et al., "The evolutionary history of methicillin-resistant *Staphylococcus aureus* (MRSA)," *Proc. Natl. Acad. Sci. USA*, 2002, 99(11):7687-7692.

Guignard et al., "β-lactams against methicillin-resistant *Staphylococcus aureus*," *Curr. Opin. Pharmacol.*, 2005, 5(5):479-489.

Hougardy et al., "Direct and fast detection of methicillin resistant *Staphylococcus aureus* carriage by automated nucleic acid extraction and real time PCR," *Pathologie Biologie*, 2006, 54:477-481.

Huletsky et al., "New Real-Time PCR Assay for Rapid Detection of Methicillin-Resistant *Staphyolcoccus aureus* Directly from Specimens Containing a Mixture of Staphylococci," *J. Clin. Microbiol.*, 2004, 42(5):1875-1884.

Ito et al., "Novel Type V Staphylococcal Cassette Chromosome *mec* Driven by a Novel Cassette Chromosome Recombinase, *ccrC*," *Antimicrob. Agents Chemother.*, 2004, 48(7):2637-2651.

Jakobi et al., "Filter-Supported Preparation of λ Phage DNA," *Anal. Biochem.*, 1988, 175:196-201.

Johnson et al., "Surveillance and epidemiology of MRSA bacteraemia in the UK," *J. Antimicrob Chemother.*, 2005, 56(3):455-462.

Marko et al., "A Procedure for the Large-Scale Isolation of Highly Purified Plasmid DNA Using Alkaline Extraction and Binding to Glass Powder," *Anal. Biochem.*, 1982, 121:382-387.

Pearson and Lipman, "Improved tools for biological sequence comparison," *Proc. Natl. Acad. Sci. USA*, 1988, 85:2444-2448.

Uhl et al., "Use of the Roche LightCycler Strep B Assay for Detection of Group B *Streptococcus* from Vaginal and Rectal Swabs," *J. Clin. Microbiol.*, 2005, 43(8):4046-4051.

Uhlmann and Peyman, "Antisense Oligonucleotides: A New Therapeutic Principle," *Chemical Reviews*, 1990, 90(4):543-584.

Verma and Eckstein, "Modified Oligonucleotides: Synthesis and Strategy for Users," *Biochem.*, 1998, 67:99-134.

Vogelstein and Gillespie, "Preparative and analytical purification of DNA from agarose," *Proc. Natl. Acad. Sci. USA*, 1979, 76(2): 615-619.

Walsh, "Acyl Transfers to Water: Endopeptidases and Exopeptidases," *Enzymatic Reaction Mechanisms*, 1979, W.H. Freeman & Co., San Francisco, Chapter 3.

Zhang et al., "Novel Multiplex PCR Assay for Characterization and Concomitant Subtyping of Staphylococcal Cassette Chromosome *mec* Types I to V in Methicillin-Resistant *Staphylococcus aureus*," *J. Clin. Microbiol.*, 2005, 43(10):5026-5033.

Authorized officer Agnes Wittmann-Regis, International Preliminary Report on Patentability in PCT/EP2007/011458 mailed Jul. 9, 2009, 14 pages.

Huletsky et al., "Identification of methicillin-resistant *Staphylococcus aureus* carriage in less than 1 hour during a hospital surveillance program," *Clin. Infect. Dis.*, 2005, 40:976-981.

International Search Report in PCT/EP2007/011458 dated Apr. 15, 2008.

GenBank Accession No. AB121219 dated Jul. 2004.

* cited by examiner

RE2:
TTTGCTTCACTATAAGTATTCAGTATAAAGAATATTTCGCTATTATTTACT
TGAAATGAAAGACTGCGGAGGCTAACTATGTCAAAAATCATGAACCTCATT
ACTTATGATAAGCTTCTTAAAAACATAACAGCAATTCACATAAACCTCATA
TGTTCTGATACATTCAAAATCCCTTTATGAAGCGGCTGAAAAAACCGCATC
ATTTGATATGCTTCTTAAAAACATAACAGCAATTCACATAAACCTCATATG
TTCTGATACATTCAAAATCCCTTTATGAAGCGGCTGAAAAAACCGCATCAT
TTATGATATGCTTCT CC orfX ⟶

RE3:
CATTCTTTCTTGATTCCATTAGTTTAAATTTAAAATTTCATCATCAATTTC
TTAATTTAATTGTAGTTCCATAATCAATATAATTTGTACAGTTATTATATA
TTCTAGATCATCAATAGTTGAAAAATGGTTTATTAAACACTCTATAAACAT
CGTATGATATTGCAAGGTATAATCCAATATTTCATATATGTAATTCCTCCA
CATCTCATTAAATTTTAAATTATACACAACCTAATTTTTAGTTTTATTTA
TGATACGCTTCT CC orfX ⟶

RE7:
CAAAAAATATATTTACTTTAGTCAAATCATCTTCACTAGTGTAATTATCGA
ATGATTTATAACTAACATTTTCTAATTTATTTAACATAAAATCAATCCTTT
TTATATTTAAAATATATTATACACAATCCGTTTTTTAGTTTTATTTATGAT
ACGCCTCT CC orfX ⟶ orfX (SEQ ID NO:77):
CCACGCATAATCTTAAATGCTCTGTACACTTGTTCAATTAACACAACCCGC
ATCATTTGATGTGGGAATGTCATTTTGCTGAATGATAGTGCGTAGTTACTG
CGTTGTAAGACGTCCTTGTGCAGGCCGTTTGATCCGCCAATGACGAATACA
AAGTCGCTTTGCCCTTGGGTCATGCGTTGGTTC A ATTCTTGGGCCAATCCT
TCGGAAGATAGCATCTTTCCTTGTATTTCTAATGTAATGACTGTTGATTGT

FIG. 1

(SEQ ID NO: 86)

```
TTTGCTTCAC TATAAGTATT CAGTATAAAG AATATTTCGC TATTATTTAC
                                G(1)
TTGAAATGAA AGACTGCGGA GGCTAACTAT GTCAAAAATC ATGAACCTCA

TTACTTATGA TAAGCTTCTT AAAAACATAA CAGCAATTCA CATAAACCTC

ATATGTTCTG ATACATTCAA AATCCCTTTA TGAAGCGGCT GAAAAAACCG

CATCATTTGA TATGCTTCTT AAAAACATAA CAGCAATTCA CATAAACCTC

ATATGTTCTG ATACATTCAA AATCCCTTTA TGAAGCGGCT GAAAAAACCG

CATCATTTAT GATATGCTTC TCCACGCATA ATCTTAAATG CTCTATACAC
                                (3)TG(1)         C(1)     G(7)
TTGCTCAATT AACACAACCC GCATCATTTG ATGTGGGAAT GTCATTTTGC
   T(8)                                     A(2)
TGAATGATAG TGCGTAGTTA CTGCGTTGTA AGACGTCCTT GTGCAGGCCG
  A(1)        A(1)        A(3)
TTTGATCCGC CAATGACGAA TACAAAGTCG CTTTGCCCTT GGGTCATGCG
                                A(3)
TTGGTTCAAT TCTTGGGCCA ATCCTTCGGA AGATAGCATC TTTCCTTGTA
                    T(1)
TTTCTAATGT AATGACTGTG GATTGTGGTT TAATTTTGGC TAGTATTCGT
                  T(3)          (9)G :(1)
TGGCCTTCTT TTTCTTTTAC TTGCTCAATT TCTTTGTCGC TCA
                                       G(2)
```

FIG.2

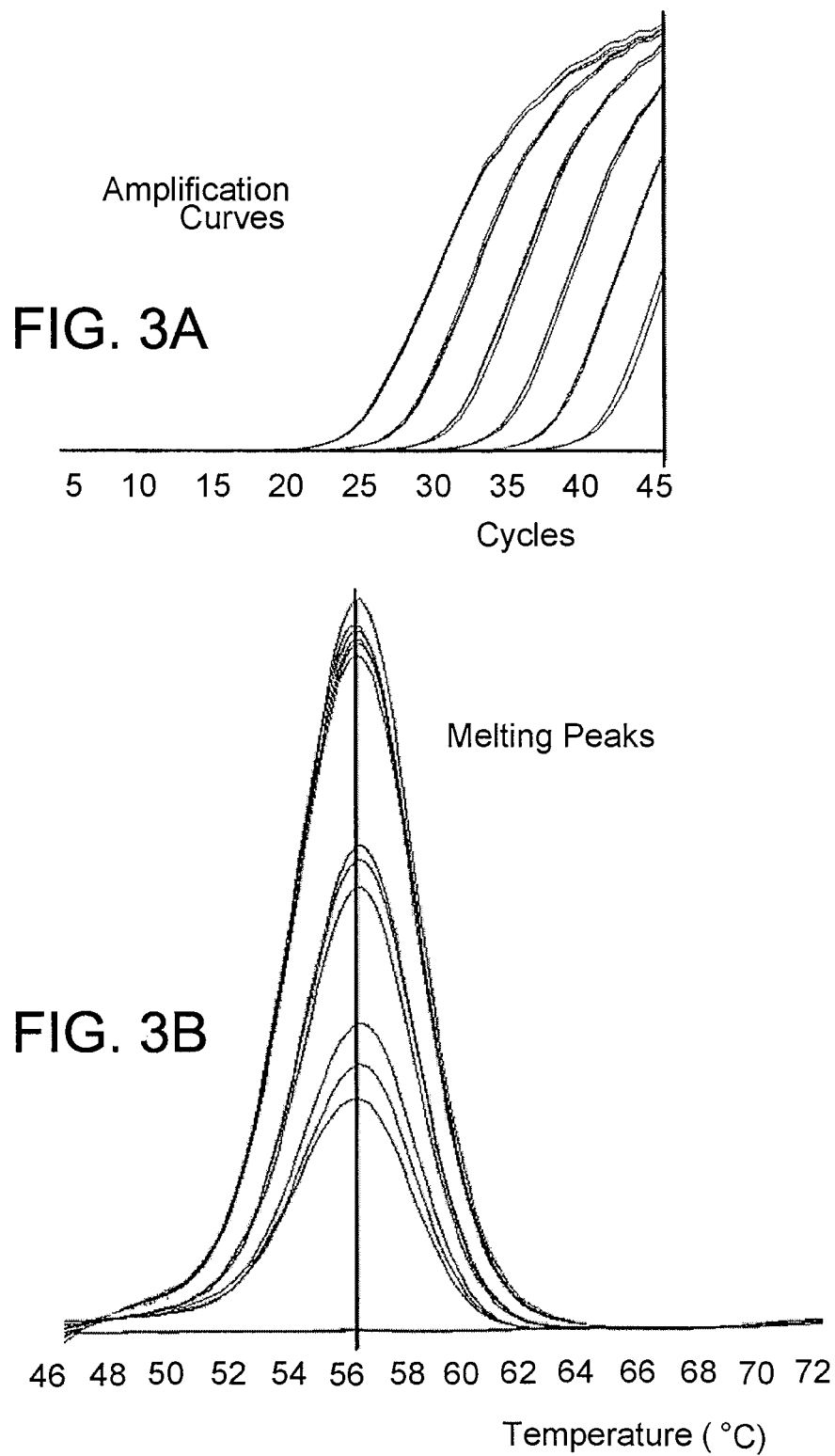
FIG. 3A Amplification Curves
FIG. 3B Melting Peaks

SEQUENCE LISTING

<160> NUMBER OF SEQ ID NOS: 98

<210> SEQ ID NO 1
<211> LENGTH: 26
<212> TYPE: DNA
<213> ORGANISM: Artificial
<220> FEATURE:
<223> OTHER INFORMATION: AR mec 1 fwd

<400> SEQUENCE: 1
gcaattcaca taaacctcat atgttc        26

<210> SEQ ID NO 2
<211> LENGTH: 24
<212> TYPE: DNA
<213> ORGANISM: Artificial
<220> FEATURE:
<223> OTHER INFORMATION: AR mec 2 fwd

<400> SEQUENCE: 2
acctcatatg ttctgataca ttca        24

<210> SEQ ID NO 3
<211> LENGTH: 22
<212> TYPE: DNA
<213> ORGANISM: Artificial
<220> FEATURE:
<223> OTHER INFORMATION: AR mec 3 fwd

<400> SEQUENCE: 3
gcaattcaca taaacctcat at        22

<210> SEQ ID NO 4
<211> LENGTH: 25
<212> TYPE: DNA
<213> ORGANISM: Artificial
<220> FEATURE:
<223> OTHER INFORMATION: AR mec 4 fwd

<400> SEQUENCE: 4
cataacagca attcacataa acctc        25

<210> SEQ ID NO 5
<211> LENGTH: 22
<212> TYPE: DNA
<213> ORGANISM: Artificial
<220> FEATURE:
<223> OTHER INFORMATION: AR mec 5 fwd -continued

<400> SEQUENCE: 5
taacagcaat tcacataaac ct                                    22

<210> SEQ ID NO 6
<211> LENGTH: 27
<212> TYPE: DNA
<213> ORGANISM: Artificial
<220> FEATURE:
<223> OTHER INFORMATION: AR mec 6 fwd

<400> SEQUENCE: 6
cgctattatt tacttgaaat gaaagac                               27

<210> SEQ ID NO 7
<211> LENGTH: 21
<212> TYPE: DNA
<213> ORGANISM: Artificial
<220> FEATURE:
<223> OTHER INFORMATION: AR mec 7 fwd

<400> SEQUENCE: 7
cttgaaatga agactgcgg a                                      21

<210> SEQ ID NO 8
<211> LENGTH: 30
<212> TYPE: DNA
<213> ORGANISM: Artificial
<220> FEATURE:
<223> OTHER INFORMATION: AR mec 8 fwd

<400> SEQUENCE: 8
ttgcttcact ataagtattc agtataaaga                            30

<210> SEQ ID NO 9
<211> LENGTH: 24
<212> TYPE: DNA
<213> ORGANISM: Artificial
<220> FEATURE:
<223> OTHER INFORMATION: AR mec 9 fwd

<400> SEQUENCE: 9
atttacttga aatgaaagac tgcg                                  24

<210> SEQ ID NO 10
<211> LENGTH: 29
<212> TYPE: DNA
<213> ORGANISM: Artificial
<220> FEATURE:
<223> OTHER INFORMATION: AR mec 10 fwd

<400> SEQUENCE: 10
aaagaatatt tcgctattat ttacttgaa                             29

<210> SEQ ID NO 11
<211> LENGTH: 29
<212> TYPE: DNA
<213> ORGANISM: Artificial
<220> FEATURE:
<223> OTHER INFORMATION: AR mec 11 fwd

<400> SEQUENCE: 11
tcagtataaa gaatatttcg ctattattt                             29

<210> SEQ ID NO 12
<211> LENGTH: 20

```
<212> TYPE: DNA
<213> ORGANISM: Artificial
<220> FEATURE:
<223> OTHER INFORMATION: AR mec 12 fwd

<400> SEQUENCE: 12
tgaaatgaaa gactgcggag                                              20

<210> SEQ ID NO 13
<211> LENGTH: 27
<212> TYPE: DNA
<213> ORGANISM: Artificial
<220> FEATURE:
<223> OTHER INFORMATION: JU1 fwd

<400> SEQUENCE: 13
aacctcatat gttctgatac attcaaa                                      27

<210> SEQ ID NO 14
<211> LENGTH: 28
<212> TYPE: DNA
<213> ORGANISM: Artificial
<220> FEATURE:
<223> OTHER INFORMATION: JU2 fwd

<400> SEQUENCE: 14
tatgtcaaaa atcatgaacc tcattact                                     28

<210> SEQ ID NO 15
<211> LENGTH: 25
<212> TYPE: DNA
<213> ORGANISM: Artificial
<220> FEATURE:
<223> OTHER INFORMATION: JU3 fwd

<400> SEQUENCE: 15
cataacagca attcacataa acctc                                        25

<210> SEQ ID NO 16
<211> LENGTH: 17
<212> TYPE: DNA
<213> ORGANISM: Artificial
<220> FEATURE:
<223> OTHER INFORMATION: JU4 fwd

<400> SEQUENCE: 16
gactgcggag gctaact                                                 17

<210> SEQ ID NO 17
<211> LENGTH: 18
<212> TYPE: DNA
<213> ORGANISM: Artificial
<220> FEATURE:
<223> OTHER INFORMATION: JU5 fwd

<400> SEQUENCE: 17 atcccttat gaagcggc                                                 18

<210> SEQ ID NO 18
<211> LENGTH: 30
<212> TYPE: DNA
<213> ORGANISM: Artificial
<220> FEATURE:
<223> OTHER INFORMATION: AR mecA 3/1

<400> SEQUENCE: 18
gcaaggtata atccaatatt tcatatatgt                                   30
```

```
<210> SEQ ID NO 19
<211> LENGTH: 29
<212> TYPE: DNA
<213> ORGANISM: Artificial
<220> FEATURE:
<223> OTHER INFORMATION: AR mecA 3/2

<400> SEQUENCE: 19
agttccataa tcaatataat ttgtacagt                              29

<210> SEQ ID NO 20
<211> LENGTH: 23
<212> TYPE: DNA
<213> ORGANISM: Artificial
<220> FEATURE:
<223> OTHER INFORMATION: AR mecA 3/3

<400> SEQUENCE: 20
acatcgtatg atattgcaag gta                                    23

<210> SEQ ID NO 21
<211> LENGTH: 26
<212> TYPE: DNA
<213> ORGANISM: Artificial
<220> FEATURE:
<223> OTHER INFORMATION: AR mecA 3/4

<400> SEQUENCE: 21
ctttcattct tcttgattc cattag                                  26

<210> SEQ ID NO 22
<211> LENGTH: 27
<212> TYPE: DNA
<213> ORGANISM: Artificial
<220> FEATURE:
<223> OTHER INFORMATION: AR mecA 3/5

<400> SEQUENCE: 22
cactctataa acatcgtatg atattgc                                27

<210> SEQ ID NO 23
<211> LENGTH: 30
<212> TYPE: DNA
<213> ORGANISM: Artificial
<220> FEATURE:
<223> OTHER INFORMATION: AR mecA 3/6

<400> SEQUENCE: 23
ttcttaattt aattgtagtt ccataatcaa                             30

<210> SEQ ID NO 24
<211> LENGTH: 30
<212> TYPE: DNA
<213> ORGANISM: Artificial
<220> FEATURE:
<223> OTHER INFORMATION: AR mecA 3/7

<400> SEQUENCE: 24
aattatacac aacctaattt ttagttttat                             30

<210> SEQ ID NO 25
<211> LENGTH: 29
<212> TYPE: DNA
<213> ORGANISM: Artificial
<220> FEATURE:
<223> OTHER INFORMATION: AR mecA 3/8
```

-continued

<400> SEQUENCE: 25 aattttagt tttatttatg atacgcttc                                      29

<210> SEQ ID NO 26
<211> LENGTH: 30
<212> TYPE: DNA
<213> ORGANISM: Artificial
<220> FEATURE:
<223> OTHER INFORMATION: AR mecA 3/9

<400> SEQUENCE: 26
acacaaccta attttagtt ttatttatga                                     30

<210> SEQ ID NO 27
<211> LENGTH: 30
<212> TYPE: DNA
<213> ORGANISM: Artificial
<220> FEATURE:
<223> OTHER INFORMATION: AR mecA 3/10

<400> SEQUENCE: 27
tttattaaac actctataaa catcgtatga                                    30

<210> SEQ ID NO 28
<211> LENGTH: 31
<212> TYPE: DNA
<213> ORGANISM: Artificial
<220> FEATURE:
<223> OTHER INFORMATION: AR mecA 3/13

<400> SEQUENCE: 28
ccacatctca ttaaatttt aaattataca c                                   31

<210> SEQ ID NO 29
<211> LENGTH: 30
<212> TYPE: DNA
<213> ORGANISM: Artificial
<220> FEATURE:
<223> OTHER INFORMATION: AR mec 5/1

<400> SEQUENCE: 29
atattataca caatccgttt tttagtttta                                    30

<210> SEQ ID NO 30
<211> LENGTH: 29
<212> TYPE: DNA
<213> ORGANISM: Artificial
<220> FEATURE:
<223> OTHER INFORMATION: AR mec 5/2

<400> SEQUENCE: 30
acacaatccg tttttagtt ttatttatg                                      29

<210> SEQ ID NO 31
<211> LENGTH: 30
<212> TYPE: DNA
<213> ORGANISM: Artificial
<220> FEATURE:
<223> OTHER INFORMATION: AR mec 5/3

<400> SEQUENCE: 31
ttctaattta tttaacataa aatcaatcct                                    30

<210> SEQ ID NO 32
<211> LENGTH: 33

```
<212> TYPE: DNA
<213> ORGANISM: Artificial
<220> FEATURE:
<223> OTHER INFORMATION: AR mec 5/16

<400> SEQUENCE: 32 caatccttt tatatttaaa atatattata cac                              33

<210> SEQ ID NO 33
<211> LENGTH: 21
<212> TYPE: DNA
<213> ORGANISM: Artificial
<220> FEATURE:
<223> OTHER INFORMATION: AR mec 1 rev

<400> SEQUENCE: 33
aggaaagatg ctatcttccg a                                          21

<210> SEQ ID NO 34
<211> LENGTH: 21
<212> TYPE: DNA
<213> ORGANISM: Artificial
<220> FEATURE:
<223> OTHER INFORMATION: AR mec 2 rev

<400> SEQUENCE: 34
gaaagatgct atcttccgaa g                                          21

<210> SEQ ID NO 35
<211> LENGTH: 18
<212> TYPE: DNA
<213> ORGANISM: Artificial
<220> FEATURE:
<223> OTHER INFORMATION: AR mec 3 rev

<400> SEQUENCE: 35
gatgctatct tccgaagg                                              18

<210> SEQ ID NO 36
<211> LENGTH: 29
<212> TYPE: DNA
<213> ORGANISM: Artificial
<220> FEATURE:
<223> OTHER INFORMATION: AR mec 4 rev

<400> SEQUENCE: 36
gtcattacat tagaaataca aggaaagat                                  29

<210> SEQ ID NO 37
<211> LENGTH: 17
<212> TYPE: DNA
<213> ORGANISM: Artificial
<220> FEATURE:
<223> OTHER INFORMATION: AR mec 5 rev

<400> SEQUENCE: 37
gccaacgaat actagcc                                               17

<210> SEQ ID NO 38
<211> LENGTH: 24
<212> TYPE: DNA
<213> ORGANISM: Artificial
<220> FEATURE:
<223> OTHER INFORMATION: AR mec 6-2 rev

<400> SEQUENCE: 38
acgaatacta gccaaaatta aacc                                       24
```

<210> SEQ ID NO 39
<211> LENGTH: 25
<212> TYPE: DNA
<213> ORGANISM: Artificial
<220> FEATURE:
<223> OTHER INFORMATION: AR mec 7 rev

<400> SEQUENCE: 39
cacaatccac agtcattaca ttaga                                                25

<210> SEQ ID NO 40
<211> LENGTH: 22
<212> TYPE: DNA
<213> ORGANISM: Artificial
<220> FEATURE:
<223> OTHER INFORMATION: JU1 rev

<400> SEQUENCE: 40
caaggaaaga tgctatcttc cg                                                   22

<210> SEQ ID NO 41
<211> LENGTH: 29
<212> TYPE: DNA
<213> ORGANISM: Artificial
<220> FEATURE:
<223> OTHER INFORMATION: JU2 rev

<400> SEQUENCE: 41
agtcattaca ttagaaatac aaggaaaga                                            29

<210> SEQ ID NO 42
<211> LENGTH: 21
<212> TYPE: DNA
<213> ORGANISM: Artificial
<220> FEATURE:
<223> OTHER INFORMATION: JU3 rev

<400> SEQUENCE: 42
aggaaagatg ctatcttccg a                                                    21

<210> SEQ ID NO 43
<211> LENGTH: 21
<212> TYPE: DNA
<213> ORGANISM: Artificial
<220> FEATURE:
<223> OTHER INFORMATION: JU4 rev

<400> SEQUENCE: 43
aggaaagatg ctatcttccg a                                                    21

<210> SEQ ID NO 44
<211> LENGTH: 25
<212> TYPE: DNA
<213> ORGANISM: Artificial
<220> FEATURE:
<223> OTHER INFORMATION: JU5 rev

<400> SEQUENCE: 44
acaatccaca gtcattacat tagaa                                                25

<210> SEQ ID NO 45
<211> LENGTH: 22
<212> TYPE: DNA
<213> ORGANISM: Artificial
<220> FEATURE:
<223> OTHER INFORMATION: AR mec Fluo 1 w/o label

```
<400> SEQUENCE: 45
aagtcgcttt gcctttgggt ca                                          22

<210> SEQ ID NO 46
<211> LENGTH: 26
<212> TYPE: DNA
<213> ORGANISM: Artificial
<220> FEATURE:
<223> OTHER INFORMATION: AR mec Fluo 2 w/o label

<400> SEQUENCE: 46
tacaaagtcg ctttgccttt gggtca                                      26

<210> SEQ ID NO 47
<211> LENGTH: 19
<212> TYPE: DNA
<213> ORGANISM: Artificial
<220> FEATURE:
<223> OTHER INFORMATION: AR mec Fluo 3 w/o label

<400> SEQUENCE: 47
ggccgtttga tccgccaat                                              19

<210> SEQ ID NO 48
<211> LENGTH: 21
<212> TYPE: DNA
<213> ORGANISM: Artificial
<220> FEATURE:
<223> OTHER INFORMATION: AR mec Fluo 4 w/o label

<400> SEQUENCE: 48
aagtcgcttt gcccttgggt a                                           21

<210> SEQ ID NO 49
<211> LENGTH: 20
<212> TYPE: DNA
<213> ORGANISM: Artificial
<220> FEATURE:
<223> OTHER INFORMATION: AR mec Fluo 4-2 w/o label

<400> SEQUENCE: 49
aagtcgcttt gcccttgggt                                             20

<210> SEQ ID NO 50
<211> LENGTH: 22
<212> TYPE: DNA
<213> ORGANISM: Artificial
<220> FEATURE:
<223> OTHER INFORMATION: AR mec Fluo 4-3 w/o label

<400> SEQUENCE: 50
aagtcgcttt gcccttgggt ca                                          22

<210> SEQ ID NO 51
<211> LENGTH: 19
<212> TYPE: DNA
<213> ORGANISM: Artificial
<220> FEATURE:
<223> OTHER INFORMATION: AR mec Fluo 4-GV w/o label

<400> SEQUENCE: 51
aagtcgcttt gcccttggg                                              19

<210> SEQ ID NO 52
<211> LENGTH: 20
```

-continued

<212> TYPE: DNA
<213> ORGANISM: Artificial
<220> FEATURE:
<223> OTHER INFORMATION: AR mec Fluo 4k w/o label

<400> SEQUENCE: 52
caagaattga accaacgcat                                        20

<210> SEQ ID NO 53
<211> LENGTH: 30
<212> TYPE: DNA
<213> ORGANISM: Artificial
<220> FEATURE:
<223> OTHER INFORMATION: AR mec Fluo 5 w/o label

<400> SEQUENCE: 53
caatgacgaa tacatagtcg ctttgcccTT                             30

<210> SEQ ID NO 54
<211> LENGTH: 21
<212> TYPE: DNA
<213> ORGANISM: Artificial
<220> FEATURE:
<223> OTHER INFORMATION: AR mec Fluo 6 w/o label

<400> SEQUENCE: 54
cgtttgatcc gccaatgacg a                                      21

<210> SEQ ID NO 55
<211> LENGTH: 22
<212> TYPE: DNA
<213> ORGANISM: Artificial
<220> FEATURE:
<223> OTHER INFORMATION: AR mec Fluo 7 w/o label

<400> SEQUENCE: 55
gccaatcctt cggaagatag ca                                     22

<210> SEQ ID NO 56
<211> LENGTH: 18
<212> TYPE: DNA
<213> ORGANISM: Artificial
<220> FEATURE:
<223> OTHER INFORMATION: AR mec Fluo UR w/o label

<400> SEQUENCE: 56
attaacacaa cccgcatc                                          18

<210> SEQ ID NO 57
<211> LENGTH: 19
<212> TYPE: DNA
<213> ORGANISM: Artificial
<220> FEATURE:
<223> OTHER INFORMATION: JU1 probe 1 w/o label

<400> SEQUENCE: 57
gtcgctttgc ccttgggtc                                         19

<210> SEQ ID NO 58
<211> LENGTH: 20
<212> TYPE: DNA
<213> ORGANISM: Artificial
<220> FEATURE:
<223> OTHER INFORMATION: JU2 probe 1 w/o label

<400> SEQUENCE: 58
tcgctttgcc cttgggtcat                                        20

```
<210> SEQ ID NO 59
<211> LENGTH: 19
<212> TYPE: DNA
<213> ORGANISM: Artificial
<220> FEATURE:
<223> OTHER INFORMATION: JU3 probe 1 w/o label

<400> SEQUENCE: 59
ggccgtttga tccgccaat                                                19

<210> SEQ ID NO 60
<211> LENGTH: 22
<212> TYPE: DNA
<213> ORGANISM: Artificial
<220> FEATURE:
<223> OTHER INFORMATION: JU4 probe 1 w/o label

<400> SEQUENCE: 60
gtccttgtgc aggccgtttg at                                             22

<210> SEQ ID NO 61
<211> LENGTH: 24
<212> TYPE: DNA
<213> ORGANISM: Artificial
<220> FEATURE:
<223> OTHER INFORMATION: JU5 probe 1 w/o label

<400> SEQUENCE: 61
cttgggtcat gcgttggttc aatt                                           24

<210> SEQ ID NO 62
<211> LENGTH: 27
<212> TYPE: DNA
<213> ORGANISM: Artificial
<220> FEATURE:
<223> OTHER INFORMATION: AR mec 640 3 w/o label

<400> SEQUENCE: 62
cgaatacaaa gtcgctttgc ccttggg                                        27

<210> SEQ ID NO 63
<211> LENGTH: 20
<212> TYPE: DNA
<213> ORGANISM: Artificial
<220> FEATURE:
<223> OTHER INFORMATION: AR mec 640 4 w/o label

<400> SEQUENCE: 63
atgcgttggt tcaattcttg                                                20

<210> SEQ ID NO 64
<211> LENGTH: 20
<212> TYPE: DNA
<213> ORGANISM: Artificial
<220> FEATURE:
<223> OTHER INFORMATION: AR mec 610 4-3 w/o label

<400> SEQUENCE: 64
gcgttggttc aattcttggg                                                20

<210> SEQ ID NO 65
<211> LENGTH: 20
<212> TYPE: DNA
<213> ORGANISM: Artificial
<220> FEATURE:
<223> OTHER INFORMATION: AR mec 640 4k w/o label
```

<400> SEQUENCE: 65
acccaagggc aaagcgactt                                          20

<210> SEQ ID NO 66
<211> LENGTH: 24
<212> TYPE: DNA
<213> ORGANISM: Artificial
<220> FEATURE:
<223> OTHER INFORMATION: AR mec 640 5 w/o label

<400> SEQUENCE: 66
ggtaatgcgt tggttcaatt cttg                                     24

<210> SEQ ID NO 67
<211> LENGTH: 25
<212> TYPE: DNA
<213> ORGANISM: Artificial
<220> FEATURE:
<223> OTHER INFORMATION: AR mec 640 6 w/o label

<400> SEQUENCE: 67
acaaagtcgc tatgcccttg ggtca                                    25

<210> SEQ ID NO 68
<211> LENGTH: 29
<212> TYPE: DNA
<213> ORGANISM: Artificial
<220> FEATURE:
<223> OTHER INFORMATION: AR mec 640 7 w/o label

<400> SEQUENCE: 68
ctttccttgt atttctaatg taatgactg                                29

<210> SEQ ID NO 69
<211> LENGTH: 27
<212> TYPE: DNA
<213> ORGANISM: Artificial
<220> FEATURE:
<223> OTHER INFORMATION: AR mec 640 UR w/o label

<400> SEQUENCE: 69
ttgatgtggg aatgtcattt tgctgaa                                  27

<210> SEQ ID NO 70
<211> LENGTH: 25
<212> TYPE: DNA
<213> ORGANISM: Artificial
<220> FEATURE:
<223> OTHER INFORMATION: JU1 probe 2 w/o label

<400> SEQUENCE: 70
gcgttggttc aattcttggg ccaat                                    25

<210> SEQ ID NO 71
<211> LENGTH: 29
<212> TYPE: DNA
<213> ORGANISM: Artificial
<220> FEATURE:
<223> OTHER INFORMATION: JU2 probe 2 w/o label

<400> SEQUENCE: 71
gttggttcaa ttcttgggcc aatccttcg                                29

<210> SEQ ID NO 72
<211> LENGTH: 26

```
<212> TYPE: DNA
<213> ORGANISM: Artificial
<220> FEATURE:
<223> OTHER INFORMATION: JU3 probe 1 w/o label

<400> SEQUENCE: 72
cgaatacaaa gtcgctttgc ccttgg                                           26

<210> SEQ ID NO 73
<211> LENGTH: 29
<212> TYPE: DNA
<213> ORGANISM: Artificial
<220> FEATURE:
<223> OTHER INFORMATION: JU4 probe 2 w/o label

<400> SEQUENCE: 73
gccaatgacg aatacaaagt cgctttgcc                                        29

<210> SEQ ID NO 74
<211> LENGTH: 25
<212> TYPE: DNA
<213> ORGANISM: Artificial
<220> FEATURE:
<223> OTHER INFORMATION: JU5 probe 2 w/o label

<400> SEQUENCE: 74
tgggccaatc cttcggaaga tagca                                            25

<210> SEQ ID NO 75
<211> LENGTH: 20
<212> TYPE: DNA
<213> ORGANISM: Artificial
<220> FEATURE:
<223> OTHER INFORMATION: AR mec 610 4-MM2 w/o label

<400> SEQUENCE: 75
atgcgttggt tcgattcttg                                                  20

<210> SEQ ID NO 76
<211> LENGTH: 21
<212> TYPE: DNA
<213> ORGANISM: Artificial
<220> FEATURE:
<223> OTHER INFORMATION: AR mec 610 4-MM2-GV w/o label

<400> SEQUENCE: 76
catgcgttgg ttcgattctt g                                                21

<210> SEQ ID NO 77
<211> LENGTH: 255
<212> TYPE: DNA
<213> ORGANISM: Artificial
<220> FEATURE:
<223> OTHER INFORMATION: orfX

<400> SEQUENCE: 77
ccacgcataa tcttaaatgc tctgtacact tgttcaatta acacaacccg catcatttga      60
tgtgggaatg tcattttgct gaatgatagt gcgtagttac tgcgttgtaa gacgtccttg     120
tgcaggccgt ttgatccgcc aatgacgaat acaaagtcgc tttgcccttg ggtcatgcgt     180
tggttcaatt cttgggccaa tccttcggaa gatagcatct ttccttgtat ttctaatgta     240
atgactgttg attgt                                                     255

<210> SEQ ID NO 78
<211> LENGTH: 643
```

```
<212> TYPE: DNA
<213> ORGANISM: Staphylococcus aureus

<400> SEQUENCE: 78
tttgcttcac tataagtatt cagtataaag aatatttcgc tattatttac ttgaaatgaa      60
agactgcgga ggctaactat gtcaaaaatc atgaacctca ttacttatga taagcttctt     120
aaaaacataa cagcaattca cataaacctc atatgttctg atacattcaa aatcccttta     180
tgaagcggct gaaaaaaccg catcatttga tatgcttctt aaaaacataa cagcaattca     240
cataaacctc atatgttctg atacattcaa aatcccttta tgaagcggct gaaaaaaccg     300
catcatttat gatatgcttc tccacgcata atcttaaatg ctctatacac ttgctcaatt     360
aacacaaccc gcatcatttg atgtgggaat gtcattttgc tgaatgatag tgcgtagtta     420
ctgcgttgta agacgtcctt gtgcaggccg tttgatccgc caatgacgaa tacaaagtcg     480
ctttgccctt gggtcatgcg ttggttcaat tcttgggcca atccttcgga agatagcatc     540
tttccttgta tttctaatgt aatgactgtg gattgtggtt taattttggc tagtattcgt     600
tggccttctt tttcttttac ttgctcaatt tctttgtcgc tca                       643

<210> SEQ ID NO 79
<211> LENGTH: 513
<212> TYPE: DNA
<213> ORGANISM: Staphylococcus aureus

<400> SEQUENCE: 79
tttgcttcac tataagtatt cagtataaag aatatttcgc tattatttac ttgaaatgaa      60
agactgcgga ggctaactat gtcaaaaatc atgaacctca ttacttatga taagcttctt     120
aaaaacataa cagcaattca cataaacctc atatgttctg atacattcaa aatcccttta     180
tgaagcggct gaaaaaaccg catcatttat gatatgcttc tccacgcata atcttaaatg     240
ctctatacac ttgctcaatt aacacaaccc gcatcatttg atgtgggaat gtcattttgc     300
tgaatgatag tgcgtagtta ctgcgttgta agacgtcctt gtgcaggccg tttgatccgc     360
caatgacgaa tacaaagtcg ctttgccctt gggtcatgcg ttggttcaat tcttgggcca     420
atccttcgga agatagcatc tttccttgta tttctaatgt aatgactgtg gattgtggtt     480
taattttggc tagtattcgt tggccttctt ttt                                  513

<210> SEQ ID NO 80
<211> LENGTH: 411
<212> TYPE: DNA
<213> ORGANISM: Staphylococcus aureus

<400> SEQUENCE: 80
tttgcttcac tataagtatt cagtataaag aatatttcgc tattatttac ttgaaatgaa      60
agactgcgga ggctaactat gtcaaaaatc atgaacctca ttacttatga taagcttctc     120
cacgcataat cttaaatgct ctatacactt gctcaattaa cacaacccgc atcatttgat     180
gtgggaatgt cattttgctg aatgatagtc gtagttact gcgttgtaag acgtccttgt     240
gcaggccgtt tgatccgcca atgacgaata caaagtcgct ttgcccttgg gtcatgcgtt     300
ggttcaattc ttgggccaat ccttcggaag atagcatctt tccttgtatt tctaatgtaa     360
tgactgtgga ttgtggttta attttggcta gtattcgttg gccttctttt t              411

<210> SEQ ID NO 81
<211> LENGTH: 595
<212> TYPE: DNA
<213> ORGANISM: Staphylococcus aureus
```

```
<220> FEATURE:
<221> NAME/KEY: misc_feature
<222> LOCATION: (39)..(39)
<223> OTHER INFORMATION: n is a, c, g, or t

<400> SEQUENCE: 81
cattctttct tgattccatt agtttaaatt taaaatttnt catacaattt cttaatttaa      60
ttgtagttcc ataatcaata taatttgtac agttattata tattctagat catcaatagt     120 tgaaaatgg tttattaaac actctataaa catcgtatga tattgcaagg tataatccaa      180
tatttcatat atgtaattcc tccacatctc attaaatttt taattatac acaacctaat      240 ttttagtttt atttatgata cgcttctcca cgcataatct taaatgctct gtacacttgt    300
tcaattaaca caacccgcat catttgatgt gggaatgtca ttttgctgaa tgatagtgcg    360
tagttactgc gttgtaagac gtccttgtgc aggccgtttg atccgccaat gacgaataca    420
aagtcgcttt gcccttgggt catgcgttgg ttcaattctt gggccaatcc ttcggaagat    480
agcatctttc cttgtatttc taatgtaatg actgttgatt gtggtttgat tttggctagt    540
attcgttggc cttcttttc ttttacttgc tcaatttgct tgtcgtctc atatt           595

<210> SEQ ID NO 82
<211> LENGTH: 388
<212> TYPE: DNA
<213> ORGANISM: Staphylococcus aureus

<400> SEQUENCE: 82
tccatctcta ctttattgtt ttcttcaaat attatctcgt aatttacctt gttcattaaa     60 caaaaactg ataaaaaac cgcatcattt gtggtacgct tctccacgca taatcttaaa     120
tgctctgtac acttgttcaa ttaacacaac ccgcatcatt tgatgtggga atgtcatttt    180
gctgaatgat agtgcgtagt tactgcgttg taagacgtcc ttgtgcaggc cgtttgatcc    240
gccaatgacg aatacaaagt cgctttgccc ttgggtcatg cgttggttca attcttgggc    300
caatccttcg gaagatagca tctttccttg tatttctaat gtaatgactg ttgattgtgg    360
tttgattttg gctagtattc gttggcct                                       388

<210> SEQ ID NO 83
<211> LENGTH: 479
<212> TYPE: DNA
<213> ORGANISM: Staphylococcus aureus

<400> SEQUENCE: 83
agatgcctat aaactaacaa ttacaaatta ttattttgtg tttcacatta taatatatca     60
actagaatta attcttaata aaagtaatc attaaaattt aataaactct gctttatatt    120
ataaaattac ggctgaaata accgcatcat ttatgatatg cttctcctcg cataatctta    180
aatgctctat acacttgttc aattaacaca acccgcatca tttgatgtgg aatgtcatt    240 ttgctgaatg atagtgcgta gttactgcgt tgtaagacgt ccttgtgcag gccgtttgat    300
ccgccaataa cgaatacaaa gtcgctttgc ccttgggtca tgcgttggtt caattcttgg    360
gccaatcctt cggaagatag catctttcct tgtatttcta atgtaatgac tgtggattgt    420
ggtttgattt tggctagtat tcgttggcct tcttttcctt ttacttgctc gatttcttt     479

<210> SEQ ID NO 84
<211> LENGTH: 475
<212> TYPE: DNA
<213> ORGANISM: Staphylococcus aureus

<400> SEQUENCE: 84
```

```
aaaaagaagt cgatttacac accatgtatt aaataatgga aattcttaat ctttacttgt    60
acctaaatta tcaaacttaa tattcacttt ttattcttca aagatttgag ctaatttaat   120
aattttctca tatttttag ttttatttgt ggtacgcttc tcctcgcata atcttaaatg    180
ctctatacac ttgttcaatt aacacaaccc gcatcatttg atgtgggaat gtcattttgc   240
tgaatgatag tgcgtagtta ctgcgttgta agacgtcctt gtgcaggccg tttgatccgc   300
caataacgaa tacaaagtcg ctttgccctt gggtcatgcg ttggttcaat tcttgggcca   360
atccttcgga agatagcatc tttccttgta tttctaatgt aatgactgtg gattgtggtt   420
tgattttggc tagtattcgt tggccttctt tttcttttac ttgctcgatt tcttt        475
```

<210> SEQ ID NO 85  
<211> LENGTH: 477  
<212> TYPE: DNA  
<213> ORGANISM: Staphylococcus aureus
<400> SEQUENCE: 85

```
caaaaaatat atttacttta gtcaaatcat cttcactagt gtaattatcg aatgatttat    60
aactaacatt ttctaattta tttaacataa atcaatcct ttttatattt aaaatatatt    120
atacacaatc cgttttttag ttttatttat gatacgcctc tccacgcata atcttaaatg   180
ctctatacac ttgttcaatt aacacaaccc gcatcatttg atgtgggaat gtcattttgc   240
taaatgatag tgcatagtta ctgcgttgta agacgtcctt gtgcaggccg tttgatccgc   300
caatgacgaa tacaaagtcg ctttgccctt gggtcatgcg ttggttcaat tcttgggcca   360
atccttcgga agatagcatc tttccttgta tttctaatgt aatgactgtg gattgtggtt   420
tgattttggc tagtattcgt tggccttctt tttcttttac ttgctcaatt tctttgt      477
```

<210> SEQ ID NO 86  
<211> LENGTH: 643  
<212> TYPE: DNA  
<213> ORGANISM: Staphylococcus aureus  
<220> FEATURE:  
<221> NAME/KEY: misc_feature  
<222> LOCATION: (21)..(21)  
<223> OTHER INFORMATION: n = c or g  
<220> FEATURE:  
<221> NAME/KEY: misc_feature  
<222> LOCATION: (322)..(322)  
<223> OTHER INFORMATION: n = c or t  
<220> FEATURE:  
<221> NAME/KEY: misc_feature  
<222> LOCATION: (323)..(323)  
<223> OTHER INFORMATION: n = c or g  
<220> FEATURE:  
<221> NAME/KEY: misc_feature  
<222> LOCATION: (339)..(339)  
<223> OTHER INFORMATION: n = c or t  
<220> FEATURE:  
<221> NAME/KEY: misc_feature  
<222> LOCATION: (345)..(345)  
<223> OTHER INFORMATION: n = a or g  
<220> FEATURE:  
<221> NAME/KEY: misc_feature  
<222> LOCATION: (354)..(354)  
<223> OTHER INFORMATION: n = c or t  
<220> FEATURE:  
<221> NAME/KEY: misc_feature  
<222> LOCATION: (387)..(387)  
<223> OTHER INFORMATION: n = a or g  
<220> FEATURE:  
<221> NAME/KEY: misc_feature  
<222> LOCATION: (402)..(402)  
<223> OTHER INFORMATION: n = a or g  
<220> FEATURE:  
<221> NAME/KEY: misc_feature

```
<222> LOCATION: (414)..(414)
<223> OTHER INFORMATION: n = a or g
<220> FEATURE:
<221> NAME/KEY: misc_feature
<222> LOCATION: (423)..(423)
<223> OTHER INFORMATION: n = a or g
<220> FEATURE:
<221> NAME/KEY: misc_feature
<222> LOCATION: (471)..(471)
<223> OTHER INFORMATION: n = a or t
<220> FEATURE:
<221> NAME/KEY: misc_feature
<222> LOCATION: (516)..(516)
<223> OTHER INFORMATION: n = g or t
<220> FEATURE:
<221> NAME/KEY: misc_feature
<222> LOCATION: (570)..(570)
<223> OTHER INFORMATION: n = g or t
<220> FEATURE:
<221> NAME/KEY: misc_feature
<222> LOCATION: (582)..(582)
<223> OTHER INFORMATION: n = a or g
<220> FEATURE:
<221> NAME/KEY: misc_feature
<222> LOCATION: (584)..(584)
<223> OTHER INFORMATION: n = t or none
<220> FEATURE:
<221> NAME/KEY: misc_feature
<222> LOCATION: (627)..(627)
<223> OTHER INFORMATION: n = a or g

<400> SEQUENCE: 86
tttgcttcac tataagtatt nagtataaag aatatttcgc tattatttac ttgaaatgaa      60
agactgcgga ggctaactat gtcaaaaatc atgaacctca ttacttatga taagcttctt    120
aaaaacataa cagcaattca cataaacctc atatgttctg atacattcaa aatcccttta    180
tgaagcggct gaaaaaaccg catcatttga tatgcttctt aaaaacataa cagcaattca    240
cataaacctc atatgttctg atacattcaa aatcccttta tgaagcggct gaaaaaaccg    300
catcatttat gatatgcttc tnnacgcata atcttaaang ctctntacac ttgntcaatt    360
aacacaaccc gcatcatttg atgtggnaat gtcattttgc tnaatgatag tgcntagtta    420
ctncgttgta agacgtcctt gtgcaggccg tttgatccgc caatgacgaa nacaaagtcg    480
ctttgccctt gggtcatgcg ttggttcaat tcttgngcca atccttcgga agatagcatc    540
tttccttgta tttctaatgt aatgactgtn gattgtggtt tnantttggc tagtattcgt    600
tggccttctt tttctttttac ttgctcnatt tctttgtcgc tca                      643

<210> SEQ ID NO 87
<211> LENGTH: 23
<212> TYPE: DNA
<213> ORGANISM: Artificial
<220> FEATURE:
<223> OTHER INFORMATION: TP mec 1

<400> SEQUENCE: 87
aagtcgcttt gcccttgggt cat                                             23

<210> SEQ ID NO 88
<211> LENGTH: 25
<212> TYPE: DNA
<213> ORGANISM: Artificial
<220> FEATURE:
<223> OTHER INFORMATION: TP mec 2

<400> SEQUENCE: 88
tgctcaatta acacaacccg catca                                           25
```

```
<210> SEQ ID NO 89
<211> LENGTH: 33
<212> TYPE: DNA
<213> ORGANISM: Artificial
<220> FEATURE:
<223> OTHER INFORMATION: MB mec 1

<400> SEQUENCE: 89
gccgcgctgc tcaattaaca caacccgcgc ggc                                    33

<210> SEQ ID NO 90
<211> LENGTH: 32
<212> TYPE: DNA
<213> ORGANISM: Artificial
<220> FEATURE:
<223> OTHER INFORMATION: MB mec 2

<400> SEQUENCE: 90
gccgcgcatg cgttggttca attctgcgcg gc                                     32

<210> SEQ ID NO 91
<211> LENGTH: 18
<212> TYPE: DNA
<213> ORGANISM: Artificial
<220> FEATURE:
<223> OTHER INFORMATION: MRSA IC 4

<400> SEQUENCE: 91
ccagcagaat gccaacca                                                     18

<210> SEQ ID NO 92
<211> LENGTH: 20
<212> TYPE: DNA
<213> ORGANISM: Artificial
<220> FEATURE:
<223> OTHER INFORMATION: MRSA direct RE2 fwd

<400> SEQUENCE: 92
tgaaatgaaa gactgcggag                                                   20

<210> SEQ ID NO 93
<211> LENGTH: 31
<212> TYPE: DNA
<213> ORGANISM: Artificial
<220> FEATURE:
<223> OTHER INFORMATION: MRSA direct RE3 fwd

<400> SEQUENCE: 93
ccacatctca ttaaattttt aaattataca c                                      31

<210> SEQ ID NO 94
<211> LENGTH: 33
<212> TYPE: DNA
<213> ORGANISM: Artificial
<220> FEATURE:
<223> OTHER INFORMATION: MRSA direct RE7 fwd

<400> SEQUENCE: 94
caatcctttt tatatttaaa atatattata cac                                    33

<210> SEQ ID NO 95
<211> LENGTH: 22
<212> TYPE: DNA
<213> ORGANISM: Artificial
<220> FEATURE:
<223> OTHER INFORMATION: MRSA direct rev

<400> SEQUENCE: 95
```

```
caaggaaaga tgctatcttc cg                                                    22

<210> SEQ ID NO 96
<211> LENGTH: 19
<212> TYPE: DNA
<213> ORGANISM: Artificial
<220> FEATURE:
<223> OTHER INFORMATION: MRSA direct Fluos w/o label

<400> SEQUENCE: 96
aagtcgcttt gcccttggg                                                        19

<210> SEQ ID NO 97
<211> LENGTH: 21
<212> TYPE: DNA
<213> ORGANISM: Artificial
<220> FEATURE:
<223> OTHER INFORMATION: MRSA direct Red 610 w/o label

<400> SEQUENCE: 97
catgcgttgg ttcgattctt g                                                     21

<210> SEQ ID NO 98
<211> LENGTH: 20
<212> TYPE: DNA
<213> ORGANISM: Artificial
<220> FEATURE:
<223> OTHER INFORMATION: MRSA direct IC Red 670 w/o label

<400> SEQUENCE: 98
ccagcagaat gccagccaat                                                       20
```

COMPOSITIONS AND METHODS FOR DETECTING METHICILLIN-RESISTANT *S. AUREUS*

CROSS REFERENCE TO RELATED APPLICATIONS

This application claims priority under 35 U.S.C. §119(e) of U.S. provisional application Ser. No. 60/882,799, filed Dec. 29, 2006.

TECHNICAL FIELD

This invention relates to bacterial diagnostics, and more particularly to the detection of methicillin-resistant *S. aureus*.

BACKGROUND

*Staphylococcus aureus* (*S. aureus*; SA) is a bacterium, whose natural reservoir is mucous or wet/salty skin areas like the groin, anus or nose. In addition it inhabits wounds. Overall, the nose is the predominant environment for *S. aureus*. However, *S. aureus* can cause illnesses ranging from minor skin infections (such as pimples, boils, and cellulitis) and abscesses, to severe diseases such as pneumonia, meningitis, endocarditis, toxic shock syndrome (TSS), septicemia and Multi Organ Dysfunction Syndrome (MODS). Each year some 500,000 patients in American hospitals contract a staphylococcal infection.

Today, *S. aureus* has become resistant to many commonly used antibiotics. In the UK, only 2% of all *S. aureus* isolates are sensitive to penicillin with a similar picture in the rest of the world. The β-lactamase resistant-penicillins (methicillin, oxacillin, cloxacillin and flucloxacillin) were developed to treat penicillin-resistant *S. aureus* and are still used as first-line treatment. Methicillin was the first antibiotic in this class to be used (it was introduced in 1959), but only two years later, the first case of methicillin-resistant *S. aureus* (MRSA) was reported in England. MRSA may also be known as oxacillin-resistant *Staphylococcus aureus* (ORSA) and multiple-resistant *Staphylococcus aureus*, while non-methicillin resistant strains of *S. aureus* are sometimes called methicillin-susceptible *Staphylococcus aureus* (MSSA) if an explicit distinction must be made.

Despite its resistance, MRSA generally remained an uncommon finding even in hospital settings until the 1990's when the MRSA prevalence dramatically increased in hospitals where it is now endemic. Moreover, in the US there are increasing reports of outbreaks of MRSA colonisation and infection through skin contact in locker rooms and gymnasiums, even among healthy populations. MRSA also is becoming a problem in pediatrics (Johnson et al., 2005, *J Antimicrob Chemother* 56 (3):455-62). As of early 2005, the number of deaths in the United Kingdom attributed to MRSA has been estimated by various sources to lie in the area of 3000 per year (Johnson, supra).

Infections caused by MRSA show a higher lethality rate and more severe symptoms, since treatment is restricted because of the resistance to only few antibiotics. First-line treatment for MRSA is currently glycopeptide antibiotics (vancomycin and teicoplanin). However, there are number of problems with these antibiotics, mainly centered around the need for intravenous administration (there is no oral preparation available), toxicity and the need to monitor drug levels regularly by means of blood tests. There are also concerns that glycopeptide antibiotics do not penetrate very well into infected tissues (this is a particular concern with infections of the brain and meninges and in endocarditis). However, glycopeptides must not be used to treat methicillin-sensitive *S. aureus* as outcomes are inferior. Taken together, patients infected with MRSA do stay longer in hospital than patients just infected with SA.

Furthermore, unrecognized colonization with MRSA may lead to the distribution of MRSA from one patient to the other by replacing the flora of MRSA-uncolonized patients with MRSA. Colonization is eased by certain risk factors including e.g. previous antibiotic treatment, polymorbidity, and diabetes as well as previous stays in hospital.

From this, it follows that it is highly important to have a safe and reliable tool for the diagnosis and/or detection of MRSA.

Presently, the diagnosis of most skin infections is made by the pattern of symptoms and physical exam findings but it is not usually possible to know whether the infection is caused by *Staphylococcus* bacteria of any type or another bacterium, like e.g. group A Beta-hemolytic *Streptococcus* (*Streptococcus pyogenes*). To make a definitive diagnosis and to confirm that MRSA is the bacteria causing the infection, a culture can be done.

However, diagnosing MRSA using a conventional culture requires 16-72 hours, causing a delay in treatment, significantly impairs patient outcomes and may facilitate outbreaks as well as increase hospital costs.

Phenotypic analyses, such as coagulase type, enterotoxin (SE) type, production of toxic shock syndrome toxin-1 and in vitro antibiotic susceptibility, have been used routinely for MRSA strain typing.

Additionally, genotypic analysis for MRSA strains has been established, providing a more detailed classification than phenotypic analysis. In particular, pulse-field gel electrophoresis (PFGE) using restriction fragments of total genomic DNA of MRSA is an excellent method of characterization.

Alternatively, multilocus sequence typing (MLST) may be used in order to characterize isolates of bacteria by using the sequences of internal fragments of seven housekeeping genes. MLST has been developed and validated for *S. aureus* (Enright et al., 2002, *Proc. Nat. Acad. Sci. U.S.A.*, 99:7687-7692) and provides a discriminatory method that allows related strains recovered in different countries to be readily identified.

Test kits have been developed in order to detect MRSA (e.g., IDI-MRSA assay, Becton Dickinson, USA) which is an in vitro diagnostic test for the direct detection of nasal colonization by methicillin-resistant *Staphylococcus aureus* (MRSA) to help prevent and control MRSA infections in healthcare settings.

However, this kit has a series of disadvantages which limit its usefulness. First, it does not detect MRSA of Staphylococcal Chromosomal Cassette (SCC) type V, which is important as SCC type V is a previously identified type, especially present in Asia and Australia. Second, its applicability is restricted for a higher number of probes. Third, the preparation of the samples is quite complicated or difficult. Fourth, the concept used for the controls is not state of the art. Moreover, the inhibition rate is quite high and, finally, a numerousness of primers and probes used is required, resulting in a diagnostic tool, which is prone to errors. Additionally, melting curve analysis which may be used by the FRET probe assay allows a higher specificity within the output signal compared to amplification curves.

SUMMARY AND DETAILED DESCRIPTION

The present invention relates to methods of detecting the presence or absence of methicillin-resistant *S. aureus*

(MRSA) in a sample, the method comprising performing an amplifying step, a hybridizing step and a detecting step. Furthermore, the present invention relates to primers, probes and kits for the detection of MRSA.

One object of the present invention was to provide an alternative method for the detecting of MRSA, preferably an alternative method avoiding the above disadvantages.

The object of the present invention has been solved by providing a method of detecting the presence or absence of methicillin-resistant *S. aureus* (MRSA) in a sample, the method comprising (a) performing an amplifying step comprising contacting the sample with a set of MRSA primers to produce an amplification product if MRSA is present in the sample, (b) performing a hybridizing step comprising contacting the amplification product of step (a) with a pair of MRSA probes, wherein a first MRSA probe of the pair of MRSA probes is labeled with a donor fluorescent moiety and wherein a second MRSA probe of the pair of MRSA probes is labeled with a corresponding acceptor fluorescent moiety; and (c) detecting the presence or absence of fluorescence resonance energy transfer (FRET) between the donor fluorescent moiety of the first MRSA probe and the acceptor fluorescent moiety of the second MRSA probe, wherein the presence of FRET is indicative of the presence of MRSA in the sample and wherein the absence of FRET is indicative of the absence of MRSA in the sample, wherein the method is capable of detecting each of Staphylococcal Chromosomal Cassettes (SCCmec) types I to V of MRSA.

The method may be used for fast and reliable detection of MRSA in a sample. Particularly, the method may be used in order to detect MRSA in a sample or diagnose an MRSA infection of an individual, such as a patient.

Accordingly, fast detection of MRSA improves the situation of patients suffering from MRSA, e.g. by earlier treatment, prevents outbreaks of MRSA by, e.g., fast and strict application of barrier precautions for patients colonized or infected with MRSA in hospitals, and, therefore, reduces health care costs. Additionally, a limited number of primers, e.g. 3 or 4, may be used in order to detect members of all presently known SCCmec types, i.e. types I, I, III, IV and V which provides to a highly reliable tool for the detection of MRSA.

As detailed above, the method of the present invention is suitable for detection MRSA of all known Staphylococcal Chromosomal Cassettes (SCCmec) types, i.e. type I, II, III, IV and V. This is particularly important in order to choose the appropriate treatment, e.g., for a patient infected with MRSA.

The methicillin-resistance gene (mecA). MecA encodes an altered methicillin-resistant penicillin-binding protein (PBP2a or PBP2'), a penicillin binding protein with reduced affinity for β-lactam rings (the primary active-site of the β-lactam antibiotics such as penicillins, cephalosporins and carbapenems) (Guignard et al., 2005, *Curr Opin Pharmacol* 5 (5): 479-89), that is not present in susceptible strains and is believed to have been acquired from a distantly related species. MecA is carried on a mobile genetic element, the Staphylococcal Chromosomal Cassette mec (SCCmec) of MRSA strains, of which five forms have been described that differ in size and genetic composition. SCC elements also occur in sensitive *S. aureus* but do not carry the mecA gene or carry a non functional mecA gene. Such strains are a major source of false positive results, because they do have the same right extremity junction.

However, MRSA detection from nasal specimen by detecting the mecA gene and a *S. aureus* specific gene leads to low positive predictive values (PPV) due to the presence of varying amounts of both non-resistant *S. aureus* and methicillin-resistant coagulase-negative Staphylococci (MRCoNS). A combination of those is undistinguishable from MRSA, because of the presence of both targets. Depending on the prevalence of MRSA this situation leads up to 30% false positive results. For a better PPV, the chosen target needs to be unique for MRSA. The only target currently known is Staphylococcal Chromosomal Cassette (SCCmec), which amplifies the transposon integration site for the genetic element carrying the mecA gene.

SCCmec, the SCC element of MRSA (with functional mec A gene), is a transposon of a length of 16 kb-67 kb integrated into the 3' portion of the open reading frame X from *S. aureus* (orfx) containing the mecA gene. MecA encodes the PBP2a conferring resistance to methicillin and its derivatives as well as to other antibiotics. OrfX has no defined function in *S. aureus* and is unique to *S. aureus*. The integration of SCCmec creates a signature unique to MRSA.

SCCmec elements have two essential components; the ccr gene complex (ccr) and the mec gene complex (mec). The ccr gene complex is composed of ccr genes and surrounding open reading frames (ORFs), and the mec gene complex is composed of the mecA gene, regulatory genes, and insertion sequences upstream or downstream of mecA. Several mec and ccr allotypes have been found among SCCmec elements, which have led to the following classification (Ito et al., 2004, *Antimicrob Agents Chemother*, 48:2637-2651):

SCCmec of type I, with class B mec and type 1 ccr;
SCCmec of type II, with class A mec and type 2 ccr;
SCCmec of type III, with class A mec and type 3 ccr;
SCCmec of type IV, with class B mec and type 2 ccr; and
SCCmec of type V, with class C2 mec and type 5 ccr.

Classification of MRSA and assignment to SCCmec type I to V is a phenotypic approach. Alternatively, an approach using different genotypes of MRSA may be used. One target for MRSA detection and classification based on genotypes may be the right extremity junction (RE) of the SCCmec. This alternative method of MRSA typing relates is therefore called RE (right extremity of SCCmec) typing. This typing method takes advantage of the polymorphism at the right extremity of SCCmec DNAs adjacent to the integration site among the three types of SCCmec. On the basis of the presence or absence of nucleic acid sequences of SEQ ID NO: 78 to 85, MRSA may be classified as follows:

```
RE2 Type A (GenBank gi|73537130|gb|DQ106887.1|;
SEQ ID NO: 78)
TTTGCTTCACTATAAGTATTCAGTATAAAGAATATTTCGCTATTATTTAC

TTGAAATGAAAGACTGCGGAGGCTAACTATGTCAAAAATCATGAACCTCA

TTACTTATGATAAGCTTCTTAAAAACATAACAGCAATTCACATAAACCTC

ATATGTTCTGATACATTCAAAATCCCTTTATGAAGCGGCTGAAAAAACCG

CATCATTTGATATGCTTCTTAAAAACATAACAGCAATTCACATAAACCTC

ATATGTTCTGATACATTCAAAATCCCTTTATGAAGCGGCTGAAAAAACCG

CATCATTTATGATATGCTTCTCCACGCATAATCTTAAATGCTCTATACAC

TTGCTCAATTAACACAACCCGCATCATTTGATGTGGGAATGTCATTTTGC

TGAATGATAGTGCGTAGTTACTGCGTTGTAAGACGTCCTTGTGCAGGCCG

TTTGATCCGCCAATGACGAATACAAAGTCGCTTTGCCCTTGGGTCATGCG
```

-continued

TTGGTTCAATTCTTGGGCCAATCCTTCGGAAGATAGCATCTTTCCTTGTA

TTTCTAATGTAATGACTGTGGATTGTGGTTTAATTTTGGCTAGTATTCGT

TGGCCTTCTTTTTCTTTTACTTGCTCAATTTCTTTGTCGCTCA

RE2_Type_B (GenBank gi|73537130|gb|DQ106887.1|;
SEQ ID NO: 79)
TTTGCTTCACTATAAGTATTCAGTATAAAGAATATTTCGCTATTATTTAC

TTGAAATGAAAGACTGCGGAGGCTAACTATGTCAAAAATCATGAACCTCA

TTACTTATGATAAGCTTCTTAAAAACATAACAGCAATTCACATAAACCTC

ATATGTTCTGATACATTCAAAATCCCTTTATGAAGCGGCTGAAAAAACCG

CATCATTTATGATATGCTTCTCCACGCATAATCTTAAATGCTCTATACAC

TTGCTCAATTAACACAACCCGCATCATTTGATGTGGGAATGTCATTTTGC

TGAATGATAGTGCGTAGTTACTGCGTTGTAAGACGTCCTTGTGCAGGCCG

TTTGATCCGCCAATGACGAATACAAAGTCGCTTTGCCCTTGGGTCATGCG

TTGGTTCAATTCTTGGGCCAATCCTTCGGAAGATAGCATCTTTCCTTGTA

TTTCTAATGTAATGACTGTGGATTGTGGTTTAATTTTGGCTAGTATTCGT

TGGCCTTCTTTTT

RE2_Type_C (GenBank gi|57284222|gb|CP000046.1|;
SEQ ID NO: 80)
TTTGCTTCACTATAAGTATTCAGTATAAAGAATATTTCGCTATTATTTAC

TTGAAATGAAAGACTGCGGAGGCTAACTATGTCAAAAATCATGAACCTCA

TTACTTATGATAAGCTTCTCCACGCATAATCTTAAATGCTCTATACACTT

GCTCAATTAACACAACCCGCATCATTTGATGTGGGAATGTCATTTTGCTG

AATGATAGTGCGTAGTTACTGCGTTGTAAGACGTCCTTGTGCAGGCCGTT

TGATCCGCCAATGACGAATACAAAGTCGCTTTGCCCTTGGGTCATGCGTT

GGTTCAATTCTTGGGCCAATCCTTCGGAAGATAGCATCTTTCCTTGTATT

TCTAATGTAATGACTGTGGATTGTGGTTTAATTTTGGCTAGTATTCGTTG

GCCTTCTTTTT

RE3 (GenBank gi|23451317|gb|AF422696.1|;
SEQ ID NO: 81)
CATTCTTTCTTGATTCCATTAGTTTAAATTTAAAATTTNTCATACAATTT

CTTAATTTAATTGTAGTTCCATAATCAATATAATTTGTACAGTTATTATA

TATTCTAGATCATCAATAGTTGAAAAATGGTTTATTAAACACTCTATAAA

CATCGTATGATATTGCAAGGTATAATCCAATATTTCATATATGTAATTCC

TCCACATCTCATTAAATTTTTAAATTATACACAACCTAATTTTTAGTTTT

ATTTATGATACGCTTCTCCACGCATAATCTTAAATGCTCTGTACACTTGT

TCAATTAACACAACCCGCATCATTTGATGTGGGAATGTCATTTTGCTGAA

TGATAGTGCGTAGTTACTGCGTTGTAAGACGTCCTTGTGCAGGCCGTTTG

ATCCGCCAATGACGAATACAAAGTCGCTTTGCCCTTGGGTCATGCGTTGG

TTCAATTCTTGGGCCAATCCTTCGGAAGATAGCATCTTTCCTTGTATTTC

TAATGTAATGACTGTTGATTGTGGTTTGATTTTGGCTAGTATTCGTTGGC

CTTCTTTTTCTTTTACTTGCTCAATTTGCTTTGTCGTCTCATATT

RE4 (GenBank AY267374_; SEQ ID NO: 82)
TCCATCTCTACTTTATTGTTTTCTTCAAATATTATCTCGTAATTTACCTT

GTTCATTAAACAAAAAACTGGATAAAAAACCGCATCATTTGTGGTACGCT

TCTCCACGCATAATCTTAAATGCTCTGTACACTTGTTCAATTAACACAAC

CCGCATCATTTGATGTGGGAATGTCATTTTGCTGAATGATAGTGCGTAGT

TACTGCGTTGTAAGACGTCCTTGTGCAGGCCGTTTGATCCGCCAATGACG

AATACAAAGTCGCTTTGCCCTTGGGTCATGCGTTGGTTCAATTCTTGGGC

CAATCCTTCGGAAGATAGCATCTTTCCTTGTATTTCTAATGTAATGACTG

TTGATTGTGGTTTGATTTTGGCTAGTATTCGTTGGCCT

RE5 (GenBank AY267381; SEQ ID NO: 83)
AGATGCCTATAAACTAACAATTACAAATTATTATTTTGTGTTTCACATTA

TAATATATCAACTAGAATTAATTCTTAATAAAAAGTAATCATTAAAATTT

AATAAACTCTGCTTTATATTATAAAATTACGGCTGAAATAACCGCATCAT

TTATGATATGCTTCTCCTCGCATAATCTTAAATGCTCTATACACTTGTTC

AATTAACACAACCCGCATCATTTGATGTGGGAATGTCATTTTGCTGAATG

ATAGTGCGTAGTTACTGCGTTGTAAGACGTCCTTGTGCAGGCCGTTTGAT

CCGCCAATAACGAATACAAAGTCGCTTTGCCCTTGGGTCATGCGTTGGTT

CAATTCTTGGGCCAATCCTTCGGAAGATAGCATCTTTCCTTGTATTTCTA

ATGTAATGACTGTGGATTGTGGTTTGATTTGGCTAGTATTCGTTGGCCT

TCTTTTTCTTTTACTTGCTCGATTTCTTT

RE6 (GenBank AY267375; SEQ ID NO: 84)
AAAAAGAAGTCGATTTACACACCATGTATTAAATAATGGAAATTCTTAAT

CTTTACTTGTACCTAAATTATCAAACTTAATATTCACTTTTTATTCTTCA

AAGATTTGAGCTAAATTTAATAATTTTCTCATATTTTTTAGTTTTATTTGT

GGTACGCTTCTCCTCGCATAATCTTAAATGCTCTATACACTTGTTCAATT

AACACAACCCGCATCATTTGATGTGGGAATGTCATTTTGCTGAATGATAG

TGCGTAGTTACTGCGTTGTAAGACGTCCTTGTGCAGGCCGTTTGATCCGC

CAATAACGAATACAAAGTCGCTTTGCCCTTGGGTCATGCGTTGGTTCAAT

TCTTGGGCCAATCCTTCGGAAGATAGCATCTTTCCTTGTATTTCTAATGT

AATGACTGTGGATTGTGGTTTGATTTTGGCTAGTATTCGTTGGCCTTCTT

TTTCTTTTACTTGCTCGATTTCTTT

RE7 (GenBank gi|49257031|dbj|AB121219.1|,
SEQ ID NO: 85)
CAAAAAATATATTTACTTTAGTCAAATCATCTTCACTAGTGTAATTATCG

AATGATTTATAACTAACATTTTCTAATTTATTTAACATAAAATCAATCCT

TTTTATATTTAAAATATATTATACACAATCCGTTTTTTAGTTTTATTTAT

GATACGCCTCTCCACGCATAATCTTAAATGCTCTATACACTTGTTCAATT

AACACAACCCGCATCATTTGATGTGGGAATGTCATTTTGCTAAATGATAG

TGCATAGTTACTGCGTTGTAAGACGTCCTTGTGCAGGCCGTTTGATCCGC

CAATGACGAATACAAAGTCGCTTTGCCCTTGGGTCATGCGTTGGTTCAAT

TCTTGGGCCAATCCTTCGGAAGATAGCATCTTTCCTTGTATTTCTAATGT

AATGACTGTGGATTGTGGTTTGATTTTGGCTAGTATTCGTTGGCCTTCTT

TTTCTTTTACTTGCTCAATTTCTTTGT

As detailed above, RE types describe the sequence variations of the right extremity junction of the SCCmec transposon. RE2 constitutes the majority of all RE types (representing SCCmec types I, II, III (some) and some IV). RE3 and RE7 represent SCCmec types III and V, and SCCmec types V, respectively.

Accordingly, in one embodiment of the invention, a particular set of primers is used in order to provide for detection of all SCCmec types. The set of primers may comprise
i. at least one primer specific for MRSA type RE2 such as a primer comprising or consisting of a nucleic acid sequence selected from the group consisting of:

```
                                 (AR mec1 fwd; SEQ ID NO: 1)
5'- GCA ATT CAC ATA AAC CTC ATA TGT TC -3', (AR mec2 fwd; SEQ ID NO: 2)
5'- ACC TCA TAT GTT CTG ATA CAT TCA -3', (AR mec3 fwd; SEQ ID NO: 3)
5'- GCA ATT CAC ATA AAC CTC ATA T -3', (AR mec4 fwd; SEQ ID NO: 4)
5'- CAT AAC AGC AAT TCA CAT AAA CCT C -3', (AR mec5 fwd; SEQ ID NO: 5)
5'- TAA CAG CAA TTC ACA TAA ACC T -3', (AR mec 6 fwd; SEQ ID NO: 6)
5'- CGC TAT TAT TTA CTT GAA ATG AAA GAC -3', (AR mec 7 fwd; SEQ ID NO: 7)
5'- CTT GAA ATG AAA GAC TGC GGA -3', (AR mec 8 fwd; SEQ ID NO: 8)
5'- TTG CTT CAC TAT AAG TAT TCA GTA AAA GA -3', (AR mec 9 fwd; SEQ ID NO: 9)
5'- ATT TAC TTG AAA TGA AAG ACT GCG -3', (AR mec 10 fwd; SEQ ID NO: 10)
5'- AAA GAA TAT TTC GCT ATT ATT TAC TTG AA -3', (AR mec 11 fwd; SEQ ID NO: 11)
5'- TCA GTA AAA GAA TAT TTC GCT ATT ATT TT -3', (AR mec 12 fwd; SEQ ID NO: 12)
5'- TGA AAT GAA AGA CTG CGG AG -3', (JU1 fwd; SEQ ID NO: 13)
5'- AAC CTC ATA TGT TCT GAT ACA TTC AAA -3', (JU2 fwd; SEQ ID NO: 14)
5'- TAT GTC AAA AAT CAT GAA CCT CAT TAC T -3', (JU3 fwd; SEQ ID NO: 15)
5'- CAT AAC AGC AAT TCA CAT AAA CCT C -3', (JU4 fwd; SEQ ID NO: 16)
5'- GAC TGC GGA GGC TAA CT -3', (JU5 fwd; SEQ ID NO: 17)
5'- ATC CCT TTA TGA AGC GGC -3',
and (MRSA direct RE2 fwd; SEQ ID NO: 92)
5'- TGA AAT GAA AGA CTG CGG AT -3',
``` and/or
ii. at least one primer specific for MRSA type RE3 such as a primer comprising or consisting of a nucleic acid sequence selected from the group consisting of

```
                                 (AR mecA 3/1; SEQ ID NO: 18)
5'- GCA AGG TAT AAT CCA ATA TTT CAT ATA TGT -3', (AR mecA 3/2; SEQ ID NO: 19)
5'- AGT TCC ATA ATC AAT ATA ATT TGT ACA GT -3', (AR mecA 3/3; SEQ ID NO: 20)
5'- ACA TCG TAT GAT ATT GCA AGG TA -3', (AR mecA 3/4; SEQ ID NO: 21)
5'- CTT TCA TTC TTT CTT GAT TCC ATT AG -3', (AR mecA 3/5; SEQ ID NO: 22)
5'- CAC TCT ATA AAC ATC GTA TGA TAT TGC -3', (AR mecA 3/6; SEQ ID NO: 23)
5'- TTC TTA ATT TAA TTG TAG TTC CAT AAT CAA -3', (AR mecA 3/7; SEQ ID NO: 24)
5'- AAT TAT ACA CAA CCT AAT TTT TAG TTT TAT -3', (AR mecA 3/8; SEQ ID NO: 25)
5'- AAT TTT TAG TTT TAT TTA TGA TAC GCT TC -3', (AR mecA 3/9; SEQ ID NO: 26)
5'- ACA CAA CCT AAT TTT TAG TTT TAT TTA TGA -3', (AR mecA 3/10; SEQ ID NO: 27)
5'- TTT ATT AAA CAC TCT ATA AAC ATC GTA TGA -3', (AR mecA 3/13 SEQ ID NO: 28)
5'- CCA CAT CTC ATT AAA TTT TTA AAT TAT ACA C -3',
and (MRSA direct RE3 fwd; SEQ ID NO: 93)
5'- CCA CAT CTC ATT AAA TTT TTA AAT TAT ACA C-3',
``` and/or
iii. at least one primer specific for MRSA type RE7 such as a primer comprising or consisting of a nucleic acid sequence selected from the group consisting of

```
                                 (AR mec 5/1, SEQ ID NO: 29)
5'- ATA TTA TAC ACA ATC CGT TTT TTA GTT TTA -3', (AR mec 5/2, SEQ ID NO: 30)
5'- ACA CAA TCC GTT TTT TAG TTT TAT TTA TG -3', (AR mec 5/3, SEQ ID NO: 31)
5'- TTC TAA TTT ATT TAA CAT AAA ATC AAT CCT -3', (AR mec 5/16 SEQ ID NO: 32)
5'- CAA TCC TTT TTA TAT TTA AAA TAT ATT ATA CAC -3',
and (MRSA direct RE7 fwd; SEQ ID NO: 94)
5'- CAA TCC TTT TTA TAT TTA AAA TAT ATT ATA CAC-3'.
```

It is noted that the following primers are particularly suitable for use in the methods of the invention: AR mec 11 fwd, AR mec 12 fwd or MRSA direct RE2 fwd; AR mecA 3/8, AR mecA 3/1, or MRSA direct RE3 fwd; and/or AR mec 5/2, AR mec 5/16, or MRSA direct RE7 fwd.

The term "primer" is used herein as known to the expert skilled in the art and refers to "oligomeric compounds" primarily to "oligonucleotides" but also to "modified oligonucleotides" that are able to "prime" DNA synthesis by a template-dependent DNA polymerase, i.e. the 3'-end of the e.g. oligonucleotide provides a free 3'-OH group whereto further "nucleotides" may be attached by a template-dependent DNA polymerase establishing 3' to 5' phosphodiester linkage whereby desoxynucleoside triphosphates are used and whereby pyrophosphate is released. Therefore, there is—except possibly for the intended function—no fundamental difference between a "primer", an "oligonucleotide" or a "probe" according to the invention.

In another embodiment of the invention, the set of primers comprises or consists of a primer specific for MRSA type RE2, a primer specific for MRSA type RE3 and a primer specific for MRSA type RE7, wherein the primers for MRSA type RE2, for MRSA type RE3 and for MRSA type RE7 can comprise or consist of a nucleic acid sequence selected from the sequences of SEQ ID NO: 1 to 17 and 92, SEQ ID NO: 18 to 28 and 93, and SEQ ID NO: 29 to 32 and 94, respectively. In one embodiment, the primers for MRSA type RE2, for MRSA type RE3 and for MRSA type RE7 can comprise or consist of the nucleic acid sequences of SEQ ID NO:11, 25, and 30, respectively, or wherein the primers for MRSA type RE2, for MRSA type RE3 and for MRSA type RE7 can comprise or consist of the nucleic acid sequences of SEQ ID NO: 12, 28, and 32, respectively. In certain embodiments, the primers for MRSA type RE2, for MRSA type RE3 and for MRSA type RE7 comprise or consist of the nucleic acid sequences of SEQ ID NO:92, 93, and 94, respectively.

In another embodiment of the invention, the set of primers additionally comprises a further primer specific for methicillin-resistant S. aureus (MRSA) as well as methicillin-sensitive S. aureus (MSSA) (primer for MRSA/MSSA). Examples of such a primer are selected from the group of primers comprising or consisting of the nucleic acid sequence selected from the group consisting of

```
                            (AR mec 1 rev, SEQ ID NO: 33)
5'- AGG AAA GAT GCT ATC TTC CGA -3', (AR mec 2 rev, SEQ ID NO: 34)
5'- GAA AGA TGC TAT CTT CCG AAG -3', (AR mec 3 rev, SEQ ID NO: 35)
5'- GAT GCT ATC TTC CGA AGG -3', (AR mec 4 rev, SEQ ID NO: 36)
5'- GTC ATT ACA TTA GAA ATA CAA GGA AAG AT -3', (AR mec 5 rev, SEQ ID NO: 37)
5'- GCC AAC GAA TAC TAG CC -3', (AR mec 6-2 rev, SEQ ID NO: 38)
5'- ACG AAT ACT AGC CAA AAT TAA ACC -3', (AR mec 7 rev, SEQ ID NO: 39)
5'- CAC AAT CCA CAG TCA TTA CAT TAG A -3', (JU1 rev, SEQ ID NO: 40)
5'- CAA GGA AAG ATG CTA TCT TCC G -3', (JU2 rev, SEQ ID NO: 41)
5'- AGT CAT TAC ATT AGA AAT ACA AGG AAA GA -3', (JU3 rev, SEQ ID NO: 42)
5'- AGGAAAGATGCTATCTTCCGA -3', (JU4 rev, SEQ ID NO: 43)
5'- AGG AAA GAT GCT ATC TTC CGA -3', (JU5 rev, SEQ ID NO: 44)
5'- ACA ATC CAC AGT CAT TAC ATT AGA A -3',
and
                            (MRSA direct rev; SEQ ID NO: 95)
5'- CAA GGA AAG ATG CTA TCT TCC G-3'
```

In one embodiment, AR mec 6-2 rev, JU1 rev or MRSA direct rev is used.

As detailed above, it is an object of the present invention to provide a highly reliable tool for the detection of MRSA. In order to reduce the susceptibility of the method of the invention to fail, the number of primers used in the method may be restricted. Accordingly, in a further embodiment of the invention, the set of primers consists of, at most 5 (e.g., at most 3 or 4 primers). Examples of such sets are:

a primer specific for MRSA type RE2, a primer specific for MRSA type RE3, and a primer specific for MRSA type RE7 (e.g., wherein one, two or three of the primers are selected from the nucleic acids of SEQ ID NO: 1 to 32 and 92 to 94), a primer specific for MRSA type RE2, a primer specific for MRSA type RE3, a primer specific for MRSA type RE7, and a primer specific for MRSA as well as MSSA (primer for MRSA/MSSA) (e.g., wherein one, two, three or four of the primers are selected from the nucleic acids of SEQ ID NO: 1 to 44 and 92 to 95), AR mec 11 fwd, AR mecA 3/8 and AR mec 512 and optionally a reverse primer, AR mec 12 fwd, AR mecA 3/13 and AR mec 5/16 and optionally a reverse primer, AR mec 11 fwd, AR mecA 3/8, AR mec 512 and AR mec 6-2 rev, AR mec 12 fwd, AR mecA 3/13, AR mec 5/16 and JU1 rev, MRSA direct RE2 fwd, MRSA direct RE3 fwd, and MRSA direct RE7 fwd and, optionally, a reverse primer, or MRSA direct RE2 fwd, MRSA direct RE3 fwd, MRSA direct RE7 fwd and MRSA direct rev.

In another embodiment of the invention, the primer for RE2, RE3, RE7 and/or MRSA/MSSA comprises or consists of a functionally active variant of any of the primers of SEQ ID NO: 1 to 44 or 92 to 95, optionally encompassed in any of the combinations of particular primers detailed above.

A functionally active variant of any of the primers of SEQ ID NO:1 to 44 or 92 to 95 may be identified by using the primer in the method of the invention. A functionally active variant of a primer of any of the SEQ ID NO: 1 to 44 or 92 to 95 pertains to a primer which provides a similar or higher specificity and sensitivity in the method or kit of the invention as compared to the respective sequence of SEQ ID NO: 1 to 44 or 92 to 95.

The term "specificity," in a binary classification test with respect to a given class, is the probability that the test correctly classifies cases not belonging to that class. That is, "specificity" is the proportion of true negatives of all negative cases in the population, and is a parameter of the test. For the detection of MRSA in the present case, the specificity to the presence of MRSA is the probability that if MRSA is absent, the test will be negative.

$$\text{specificity} = \frac{\text{number of true negatives}}{\text{number of true negatives} + \text{number of false positives}}$$

Accordingly, a specificity of 100% means that the test recognizes all MRSA positive samples as MRSA positive. A similar specificity in the context of the present invention relates to a specificity which is at most 10%, preferably at most 5%, more preferably at most 4%, 3%, 2% or 1% smaller than that of the respective primer, if the primers (the variant and respective primer without mutation) are tested in the method of the invention (e.g., the method as described in Example 3).

The term "sensitivity" in a binary classification test with respect to a given class is the probability that the test correctly classifies cases belonging to that class. That is, "sensitivity" is the proportion of true positives of all positives cases in the population and is a parameter of the test. For the detection of MRSA in the present case, the sensitivity to the presence of MRSA is the probability that if MRSA is present, the test will be positive.

$$\text{sensitivity} = \frac{\text{number of true positives}}{\text{number of true positives} + \text{number of false negatives}}$$

A sensitivity of 100% means that the test recognizes all sick people as such. It is noted that a trivial test always can be generated that achieves 100% sensitivity by classifying all test cases positive. A similar sensitivity in the context of the present invention relates to a sensitivity which is at most 10%, preferably at most 5%, more preferably at most 4%, 3%, 2% or 1% smaller than that of the respective primer, if the primers (the variant and respective primer without mutation) are tested in the method of the invention (e.g., the method as described in Example 3).

In one embodiment, the primer comprises or consists of a functionally active variant of any of the primers of SEQ ID NO: 1 to 44, wherein
  (a) the functionally active variant is a functionally active part of a primer of SEQ ID NO: 1 to 44 or 92 to 95, the part encompassing at least 70% (e.g., at least 75%, at least 80%, at least 90%, at least 95%, or at least 99%) of any of the sequences of SEQ ID NO: 1 to 44 or 92 to 95;
  (b) the functionally active variant is a functionally active variant having at least 70% (e.g., at least 75%, at least 80%, at least 85%, at least 90%, at least 95%, or at least 99%) sequence identity with any of the sequences of SEQ ID NO: 1 to 44 or 92 to 95;
  (c) the functionally active variant is a probe of SEQ ID NO: 1 to 44 or 92 to 95 comprising at least one chemically modified nucleic acid; and/or
  (d) the functionally active variant is a functionally active variant complementary to any of the sequences of SEQ ID NO: 1 to 44 or 92 to 95 or a functionally active variant of (a), (b) and/or (c).

The part of the primer may be obtained by terminal deletion of nucleotides (at the 5' end and/or the 3' end). Sequence identity may be determined by sequence alignment. Methods of alignment of sequences for comparison are well known in the art. Various programs and alignment algorithms have been described, e.g., in Smith & Waterman, 1981, *Adv. Appl. Math.* 2: 482; or Pearson & Lipman, 1988, *Proc. Natl. Acad. Sci. U.S.A.*, 85: 2444-2448.

The NCBI Basic Local Alignment Search Tool (BLAST) (Altschul et al., 1990, *J. Mol. Biol.* 215:403-410) is available from several sources, including the National Center for Biotechnology Information (NCBI, Bethesda, Md.) and on the Internet, for use in connection with the sequence analysis programs BLASTP, BLASTN, BLASTX, TBLASTN and TBLASTX. Variants of a primer of any of the sequences of SEQ ID NO: 1 to 44 or 92 to 95 are typically characterized using NCBI BLAST.

The variant may, e.g., vary from the sequence of SEQ ID NO: 1 to 44 or 92 to 95 by one or more nucleotide additions, deletions or substitutions such as one or more nucleotide additions, deletions or substitutions at the 5' end and/or the 3' end of the respective sequence of SEQ ID NO: 1 to 44 or 92 to 95. As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

A "modified oligonucleotide" (or "oligonucleotide analog") belongs to another specific subgroup of "oligomeric compounds" that possesses one or more "nucleotides", one or more "non-nucleotide compounds" or "modified nucleotides" as "monomeric units". Thus, the terms "modified oligonucleotide" (or "oligonucleotide analog") refer to structures that function in a manner substantially similar to "oligonucleotides" and are used interchangeably throughout the application. A "modified oligonucleotide" (or a "oligonucleotide analog") also can be, for example, made by chemical modification of "oligonucleotides" by appropriate modification of the phosphate backbone, ribose unit or the nucleotide bases (see, for example, Uhlmann & Peyman, 1990, *Chemical Reviews*, 90:543; and Verma & Eckstein, 1998, *Annu. Rev. Biochem.*, 67:99-134). Representative modifications include phosphorothioate, phosphorodithioate, methyl phosphonate, phosphotriester or phosphoramidate inter-nucleoside linkages in place of phosphodiester inter-nucleoside linkages; deaza or aza purines and pyrimidines in place of natural purine and pyrimidine bases, pyrimidine bases having substituent groups at the 5 or 6 position; purine bases having altered substituent groups at the 2, 6 or 8 positions or 7 position as 7-deazapurines; sugars having substituent groups at, for example, their 2' position; or carbocyclic or acyclic sugar analogs. Other modifications consistent with the spirit of this invention are known to those skilled in the art. Such "modified oligonucleotides" (or "oligonucleotide analogs") are best described as being functionally interchangeable with, yet structurally different from, natural "oligonucleotides" (or synthetic "oligonucleotides" along natural lines). In more detail, exemplary modifications are disclosed in Verma & Eckstein, 1998, *Annu. Rev. Biochem.*, 67:99-134 or WO 02/12263. In addition, modification can be made wherein nucleoside units are joined through groups that substitute for the internucleoside phosphate or sugar phosphate linkages. Such linkages include those disclosed in Verna & Eckstein, supra. When other than phosphate linkages are utilized to link the nucleoside units, such structures have also been described as "oligonucleosides".

Oligonucleotides including modified oligonucleotides and oligonucleotide analogs that amplify a nucleic acid molecule encoding MRSA, e.g., nucleic acids encoding alternative portions of portions of RE2, RE3 or RE7, can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g. 8, 10, 12, 14, 16, 18, 20, 22, 24, 26, 28, 30, 32, 34, 36, 38, 40, 42, 44, 46, 48, or 50 nucleotides in length).

The sequences of SCCmec of various subtypes of MRSA are available to the public, e.g., at the nucleotide database of NCBI (National Center for Biotechnology Information) (see, e.g., Accession No. AB033763 for type-I staphylococccal cassette chromosome mec, strain NCTC10442; Accession No. D86934 for type-II staphylococcal cassette chromosome mec, strain N315; Accession No. AB047089, right extremity of type-III Staphylococcal cassette chromosome mec and its flanking chromosomal region, strain 85/3907; Accession No. AB063172 for type-IV.1 (IVa) staphylococcal cassette chromosome mec, strain CA05(JCSC1968); or Accession No. AB121219 type-V staphylococcal cassette chromosome mec, strain JCSC3624(WIS)).

"Primers specific for RE2" or "primers specific for RE3" or "primers specific for RE7" as used herein refer to oligonucleotide primers that anneal to nucleic acid sequences encoding RE2 or RE3 or RE7, respectively, and initiate synthesis therefrom under appropriate conditions.

In addition to a set of primers, the methods of the invention use a pair of probes in order to detect the presence or absence of MRSA. The term "probe" refers to synthetically or biologically produced nucleic acids (DNA or RNA) which, by design or selection, contain specific nucleotide sequences that allow them to hybridize under defined predetermined stringencies specifically (i.e., preferentially) to "target nucleic acids", in the present case to a MRSA (target) nucleic acid. A "probe" can be referred to as a "detection probe" meaning that it detects the target nucleic acid.

In one embodiment of the invention, at least one probe of the pair of probes comprises or consists of a fluorescent moiety and a nucleic acid sequences selected from the group consisting of (shown without the label):

```
                       (AR mec Fluo 1; SEQ ID NO: 45)
5'- AAG TCG CTT TGC CTT TGG GTC A -3', (AR mec Fluo 2; SEQ ID NO: 46)
5'- TAC AAA GTC GCT TTG CCT TTG GGT CA -3', (AR mec Fluo 3; SEQ ID NO: 47)
5'- GGC CGT TTG ATC CGC CAA T -3', (AR mec Fluo 4; SEQ ID NO: 48)
5'- AAG TCG CTT TGC CCT TGG GTA -3', (AR mec Fluo 4-2; SEQ ID NO: 49)
5'- AAG TCG CTT TGC CCT TGG GT -3', (AR mec Fluo 4-3; SEQ ID NO: 50)
5'- AAG TCG CTT TGC CCT TGG GTC A -3', (AR mec Fluo 4-GV; SEQ ID NO: 51)
5'- AAG TCG CTT TGC CCT TGG G -3', (AR mec Fluo 4k; SEQ ID NO: 52)
5'- CAA GAA TTG AAC CAA CGC AT -3', (AR mec Fluo 5; SEQ ID NO: 53)
5'- CAA TGA CGA ATA CAT AGT CGC TTT GCC CTT -3', (AR mec Fluo 6; SEQ ID NO: 54)
5'- CGT TTG ATC CGC CAA TGA CGA -3', (AR mec Fluo 7; SEQ ID NO: 55)
5'- GCC AAT CCT TCG GAA GAT AGC A -3', (AR mec Fluo UR; SEQ ID NO: 56)
5'- ATT AAC ACA ACC CGC ATC -3', JU1 probe 1; SEQ ID NO: 57)
5'- GTC GCT TTG CCC TTG GGT C -3', JU2 probe 1; SEQ ID NO: 58)
5'- TCG CTT TGC CCT TGG GTC AT -3', JU3 probe 1; SEQ ID NO: 59)
5'- GGC CGT TTG ATC CGC CAA T -3', JU4 probe1; SEQ ID NO: 60)
5'- GTC CTT GTG CAG GCC GTT TGA T -3', JU5 probe1; SEQ ID NO: 61)
5'- CTT GGG TCA TGC GTT GGT TCA ATT -3', (AR mec 640 3; SEQ ID NO: 62)
5'- CGA ATA CAA AGT CGC TTT GCC CTT GGG -3', (AR mec 640 4; SEQ ID NO: 63)
5'- ATG CGT TGG TTC AAT TCT TG -3', (AR mec 610 4-3; SEQ ID NO: 64)
5'- GCG TTG GTT CAA TTC TTG GG -3', (AR mec 640 4k; SEQ ID NO: 65)
5'- ACC CAA GGG CAA AGC GAC TT -3', (AR mec 640 5; SEQ ID NO: 66)
5'- GGT AAT GCG TTG GTT CAA TTC TTG -3', (AR mec 640 6; SEQ ID NO: 67)
5'- ACA AAG TCG CTA TGC CCT TGG GTC A -3', (AR mec 640 7; SEQ ID NO: 68)
5'- CTT TCC TTG TAT TTC TAA TGT AAT GAC TG -3', (AR mec 640 UR; SEQ ID NO: 69)
5'- TTG ATG TGG GAA TGT CAT TTT GCT GAA -3', JU1 probe 2; SEQ ID NO: 70)
5'- GCG TTG GTT CAA TTC TTG GGC CAA T -3', JU2 probe 2; SEQ ID NO: 71)
5'- GTT GGT TCA ATT CTT GGG CCA ATC TTT CG -3', JU3 probe 2; SEQ ID NO: 72)
5'- CGA ATA CAA AGT CGC TTT GCC CTT GG -3', JU4 probe2; SEQ ID NO: 73)
5'- GCC AAT GAC GAA TAC AAA GTC GCT TTG CC -3', JU5 probe2; SEQ ID NO: 74)
5'- TGG GCC AAT CCT TCG GAA GAT AGC A -3', (AR mec 610 4-MM2; SEQ ID NO: 75)
5'- ATG CGT TGG TTC GAT TCT TG -3', (AR mec 610 4-MM2-GV; SEQ ID NO: 76)
5'- CAT GCG TTG GTT CGA TTC TTG -3', (MRSA direct Fluos; SEQ ID NO: 96)
5'- AAG TCG CTT TGC CCT TGG G-3',
and (MRSA direct Red 610; SEQ ID NO: 97)
5'- CAT GCG TTG GTT CGA TTC TTG-3'.
```

AR mec Fluo 4 and/or AR mec 610 4-MM2, AR mec Fluo 4-GV and/or AR mec 610 4-MM2-GV, and/or NRSA direct Fluos and/or MRSA direct Red 610 are suitable probes for use in the invention.

In one embodiment, the first probe can comprise or consist of a fluorescent moiety and the nucleic acid sequence of SEQ ID NO:48 and the second probe can comprise or consist of a fluorescent moiety and a nucleic acid sequence of SEQ ID NO:75 or vice versa. In one embodiment, the first probe can comprise or consist of a fluorescent moiety and the nucleic acid sequence of SEQ ID NO:51 and the second probe can comprise or consist of a fluorescent moiety and a nucleic acid sequence of SEQ ID NO:76 or vice versa. In one embodiment, the first probe comprises or consists of a fluorescent moiety and the nucleic acid sequence of SEQ ID NO:96 and the second probe comprises or consists of a fluorescent moiety and a nucleic acid sequence of SEQ ID NO:97 or vice versa. The first MRSA probe of the pair of MRSA probes can be labeled with a donor fluorescent moiety and the second MRSA probe of the pair of MRSA probes can be labeled with a corresponding acceptor fluorescent moiety. Examples of suitable and preferred labels are listed below, wherein each of the probes may be labeled with any of the labels. A representative pair of probes is one in which the first probe including the first label is fluorescein-5'-AAG TCG CTT TGC CCT TGG GTA-3' (AR mec Fluo 4; SEQ ID NO:48) and wherein the second probe including the second label is LC-Red 610-5'-ATG CGT TGG TTC GAT TCT TG-3' (AR mec 610 4-MM2; SEQ ID NO:75). An alternative representative pair of probes is one in which the first probe including the first label is fluorescein-5'-AAG TCG CTT TGC CCT TGG G-3' (AR mec Fluo 4-GV; SEQ ID NO:51) and wherein the second probe including the second label is LC-Red 610-5'-CAT GCG TTG GTT CGA TTC TTG-3' (AR mec 610 4-MM2-GV; SEQ ID NO:76). Another representative pair of probes is one in which the fist probe including the first label is 5'-AAG TCG CTT TGC CCT TGG G-3'-fluorescein (MRSA direct Fluos; SEQ ID NO:96) and the second probe including the second label is LC-Red 610-5'-CAT GCG TTG GTT CGA TTC TTG-3' (MRSA direct Red 610; SEQ ID NO:97).

In another embodiment, the probe comprises or consists of a fluorescent moiety and a functionally active variant of any of the probes of SEQ ID NO: 45 to 76, 96 or 97. For example,
 (a) the functionally active variant is a functionally active part of a probe of any of SEQ ID NOs:45 to 76, 96 or 97, the part encompassing at least 70% (e.g., at least 75%, at least 80%, at least 90%, at least 95%) of any of the sequences of SEQ ID NO: 45 to 76, 96 or 97;
 (b) the functionally active variant is a functionally active variant having at least 70% (e.g., at least 75%, at least 80%, at least 85%, at least 90%, at least 95%) sequence identity with any of the sequences of SEQ ID NO: 45 to 76, 96 or 97;
 (c) the functionally active variant is a probe of SEQ ID NO: 45 to 76, 96 or 97 comprising at least one chemically modified nucleic acid; and/or
 (d) the functionally active variant is a functionally active variant complementary to any of the sequences of SEQ ID NO: 45 to 76, 96 or 97 or a functionally active variant of (a), (b) and/or (c).

A functionally active variant of any of these probes may be identified by using the variant and the respective probe in the method of the invention. A functionally active variant of a probe comprising any of the SEQ ID NO: 45 to 76, 96 or 97 refers to a probe which has a similar or higher specificity and sensitivity as the respective sequence of SEQ ID NO: 45 to 76, 96 or 97. The terms "specificity" and "sensitivity" are as defined above for the primers and may be determined as described for the variants of primers.

The part of the probe may be obtained by terminal deletion of nucleotides (at the 5' end and/or the 3' end). Sequence identity may be determined by sequence alignment. Methods of alignment of sequences for comparison are well known in the art. Various programs and alignment algorithms have been described, e.g., in Smith & Waterman, supra; or Pearson & Lipman, supra.

The NCBI Basic Local Alignment Search Tool (BLAST) (Altschul et al., *J. Mol. Biol.* 215: 403-410, 1990) is available from several sources, including the National Center for Biotechnology Information (NCBI, Bethesda, Md.) and on the Internet, for use in connection with the sequence analysis programs BLASTP, BLASTN, BLASTX, TBLASTN and TBLASTX. Variants of a probe comprising any of the sequences of SEQ ID NO: 45 to 76, 96 or 97 are typically characterized using one or more of the NCBI BLAST programs.

The variant may, e.g., vary from the sequence of SEQ ID NO: 45 to 76, 96 or 97 by one or more nucleotide additions, deletions or substitutions, such as one or more nucleotide additions, deletions or substitutions at the 5' end and/or the 3' end of the respective sequence of SEQ ID NO: 45 to 76, 96 or 97.

Additionally, it is referred to the above details regarding variants of primers, which may be applied analogously to the variants of probes.

In one embodiment of the invention, a set of primers comprises or consists of
 a) AR mec 11 fwd, AR mecA 3/8, AR mec 512 and optionally AR mec 6-2 rev and wherein the first probe is fluorescein-5'-AAG TCG CTT TGC CCT TGG GTA-3' (AR mec Fluo 4; SEQ ID NO:48) and wherein the second probe is LC-Red 610-5'-ATG CGT TGG TTC GAT TCT TG-3' (AR mec 610 4-MM2; SEQ ID NO:75),
 b) AR mec 12 fwd, AR mecA 3/13, AR mec 5/16 and optionally JU1 rev and wherein the first probe is fluorescein-5'-AAG TCG CTT TGC CCT TGG G-3' (AR mec Fluo 4-GV; SEQ ID NO:51) and wherein the second probe including the second label is LC-Red 610-5'-CAT GCG TTG GTT CGA TTC TTG-3' (AR mec 610 4-MM2-GV; SEQ ID NO:76), or
 c) MRSA direct RE2 fwd, NRSA direct RE3 fwd, MRSA direct RE7 fwd and, optionally, MRSA direct rev, wherein the first label is 5'-AAG TCG CTT TGC CCT TGG G-3'-fluorescein (MRSA direct Fluos; SEQ ID NO:96) and wherein the second probe is LC-Red 610-5'-CAT CGC TTG GTT CGA TTC TTG-3' (MRSA direct Red 610; SEQ ID NO:97).

Designing oligonucleotides to be used as (hybridization) probes can be performed in a manner similar to the design of primers, although the members of a pair of probes preferably anneal to an amplification product within no more than 5 nucleotides of each other (e.g., within no more than 1, 2, 3, or 4 nucleotides of each other) on the same strand such that fluorescent resonance energy transfer (FRET) can occur. This minimal degree of separation typically brings the respective fluorescent moieties into sufficient proximity such that FRET occurs (see below). It is to be understood, however, that other separation distances (e.g., 6 or more nucleotides) are possible provided the fluorescent moieties are appropriately positioned relative to each other (for example, with a linker arm) such that FRET can occur. In addition, probes can be designed to hybridize to targets that contain a mutation or polymorphism, thereby allowing differential detection of MRSA based on either absolute hybridization of different pairs of probes corresponding to each particular MRSA subtype to be distinguished or differential melting temperatures between, for example, members of a pair of probes and each amplification product generated from a MRSA. As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are 8 to 50 nucleotides in length (e.g. 8, 10, 12, 14, 16, 18, 20, 22, 24, 26, 28, 30, 32, 34, 36, 38, 40, 42, 44, 46, 48, or 50 nucleotides in length).

The invention provides methods for detecting the presence or absence of MRSA in a sample. Methods provided by the invention avoid problems of sample contamination as well as false negatives and false positives. The methods include performing at least one amplifying step and at least one hybridizing step. An amplification step includes contacting the sample with a set of suitable primers to produce an amplification product if a MRSA nucleic acid molecule is present in the sample. Each of the primers anneals to a target within the MRSA target nucleic acid molecule such that at least a portion of the amplification product contains nucleic acid sequence corresponding to the respective MRSA nucleic acid, wherein the set of primers is selected to enable detection of MRSA types I to V. The hybridizing step includes contacting the sample with a pair of MRSA probes. Generally, the members of the pair of MRSA probes hybridize to the appropriate amplification product within no more than five nucleotides of each other. According to the invention, a first MRSA probe of the pair of MRSA probes is labeled with a donor fluorescent moiety and a second MRSA probe of the pair of MRSA probes is labeled with a corresponding acceptor fluorescent moiety. The method further includes detecting the presence or absence of FRET between the donor fluorescent moiety of the first MRSA probe and the corresponding acceptor fluorescent moiety of the second MRSA probe. Multiple steps of amplification and hybridization can be performed, usually in a thermocycler.

As used herein, "amplifying" refers to the process of synthesizing nucleic acid molecules that are complementary to one or both strands of a template nucleic acid (e.g., MRSA nucleic acid molecules). Amplifying a nucleic acid molecule typically includes denaturing the template nucleic acid, annealing primers to the template nucleic acid at a temperature that is below the melting temperatures of the primers, and enzymatically elongating from the primers to generate an amplification product. The denaturing, annealing and elongating steps each can be performed once. Generally, however, the denaturing, annealing and elongating steps are performed multiple times such that the amount of amplification product is increasing, oftentimes exponentially, although exponential amplification is not required by the present methods. Amplification typically requires the presence of deoxyribonucleoside triphosphates, a DNA polymerase enzyme (e.g. Taq Polymerase) and an appropriate buffer and/or co-factors for optimal activity of the polymerase enzyme (e.g., $MgCl_2$ and/or KCl).

If amplification of MRSA nucleic acid occurs and an amplification product is produced, the step of hybridizing results in a detectable signal based upon FRET between the members of the pair of probes. As used herein, "hybridizing" refers to the annealing of probes to an amplification product. Hybridization conditions typically include a temperature that is below the melting temperature of the probes but that avoids non-specific hybridization of the probes.

In the method of the invention the presence or absence of MRSA is detected using Fluorescence Resonance Energy Transfer (FRET) (see, for example, U.S. Pat. Nos. 4,996,143, 5,565,322, 5,849,489, and 6,162,603). FRET is a technique for measuring interactions between two molecules, in the present case, between two probes. In this technique, two different fluorescent molecules (fluorophores or labels) are fused to a pair of probes suitable for the detection of MRSA.

Resonance energy transfer is a mechanism by which energy is transferred directly from one molecule to another. The principle of FRET is based on the combined characteristics of the two labels. If a label is excited with a light of a particular wavelength (absorption frequency) its re-emits that energy at a different wavelength (the emission frequency). In FRET the first label is excited with which in turn emits light having the emission frequency. If the emission peak of the first label (donor) overlaps with the excitation peak of the second label (acceptor), proximity of the two labels can be determined, since the first label transfers energy to the second label and the second label emits light at its own emission frequency. The net result is that the donor emits less energy than it normally would (since some of the energy it would radiate as light gets transferred to the acceptor instead), while the acceptor emits more light energy at its excitation frequency (because it is getting extra energy input from the donor fluorophore).

The benefit of FRET technology is that it has an excellent resolution. The physics of the FRET energy transfer between donor and acceptor (which is non-radioactive) is such that the efficiency falls off with the sixth power of the distance between molecules. Thus, FRET in general occurs when the two fluorophores are within 20 to 100 Å (0.002 to 0.01 µm) of each other, which means that the fluorophores must be brought together quite closely.

As used herein, two oligonucleotide probes, each containing a fluorescent moiety, can hybridize to an amplification product at particular positions determined by the complementarity of the oligonucleotide probes to the target nucleic acid sequence, i.e., the MRSA nucleic acid. Upon hybridization of the oligonucleotide probes to the amplification product at the appropriate positions, a FRET signal is generated. In one embodiment, the members of the pair of MRSA probes (detection probes) hybridize to the amplification product within no more than five, four or three nucleotides (e.g., within no more than two nucleotides of each other or within no more than one nucleotide of each other).

As detailed above, each probe of the pair of probes is labeled with a suitable label/fluorophore/fluorescent moiety. "Labels", often referred to as "reporter groups", "fluorophores" or "fluorescent moieties", are generally groups that mark or label a target nucleic acid to make it identifiable and/or distinguishable (nucleic acids having attached a "label" can also be termed labeled nucleic acid binding compounds, labeled probes or just probes).

As used herein, "fluorescence resonance energy transfer relationship" and similar terms refer to adjacent hybridization of a "probe" labeled with a "donor fluorescent moiety" and another "probe" labeled with an "acceptor fluorescent moiety" to a "target nucleic acid" such that the "donor fluorescent label" can transfer resonance energy to the "acceptor fluorescent label" such that the "acceptor fluorescent label" produces a measurable fluorescence emission. If the "donor fluorescent label" and "acceptor fluorescent label" are spaced apart by too great a distance, then the "donor fluorescent label" cannot transfer resonance energy to the "acceptor fluorescent label" such that the "acceptor fluorescent label" emits measurable fluorescence, and hence the "donor fluorescent label" and "acceptor fluorescent label" are not in resonance energy transfer relationship.

Suitable labels are known in the art and the skilled practitioner is able to choose a suitable combination of labels for both probes. As used herein with respect to donor and corresponding acceptor fluorescent moieties, "corresponding" refers to an acceptor fluorescent moiety having an emission spectrum that overlaps the excitation spectrum of the donor fluorescent moiety. However, both signals should be separable from each other. Accordingly, the wavelength maximum of the emission spectrum of the acceptor fluorescent moiety should be at least 30 nm (e.g., at least 50 nm, at least 80 nm, at least 100 nm or at least 140 nm) greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Förster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm). However, the main target is to obtain signals separable from each other.

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothiocyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC-RED 610, LC-RED 640, LC-RED 670, LC-RED 705, Cy5, Cy5.5, Lissamine rhodamine B sulfonyl chloride, tetramethyl rhodamine isothiocyanate, rhodamine×isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

Labels according to the invention are fluorescent labels, which are, for example, fluorescent dyes as a fluorescein dye, a rhodamine dye, a cyanine dye, and a coumarin dye. For example, the donor fluorescent moiety may be fluorescein and/or the acceptor fluorescent moiety may be selected from the group consisting of LC-RED 610, LC-RED 640, LC-RED 670, LC-RED 705, Cy5, and Cy5.5.

For the donor-acceptor pair of fluorescein-rhodamine, one might use a 470-490 nm excitation filter and a 500-520 nm emission filter for collecting the light from the fluorescein donor. One might then use a 600-650 nm emission filter for collecting the light from the rhodamine acceptor. These emission filters need to collect just the shorter wavelength range of the donor, and just the long emission tail of the acceptor, to avoid cross-talk between the two image channels. That is, one would want to avoid collecting fluorescein emission in the rhodamine channel and vice versa. The problem is that for FRET to work, the donor emission and acceptor excitation spectra must overlap (high overlap is good), but for good signal-to-noise ratio imaging one must avoid collecting the "wrong" photons through a filter.

The donor and acceptor fluorescent moieties can be attached to the appropriate probe oligonucleotide via a linker arm. The length of each linker arm can be important, as the linker arms will affect the distance between the donor and the acceptor fluorescent moieties. The length of a linker arm for the purpose of the present invention is the distance in Angstroms from the nucleotide base to the fluorescent moiety. In general, a linker arm is from about 10 to about 25 Å. The linker arm may be of the kind described in WO 84/03285. WO 84/03285 also discloses methods for attaching linker arms to particular nucleotide bases, and also for attaching fluorescent moieties to a linker arm.

An acceptor fluorescent moiety such as an LC-RED 640 (—NHS-ester), LC-RED 610(—NHS-ester) or LC-RED 670 (—NHS-ester) can be combined with C6-Phosphoramidites (available from ABI (Foster City, Calif.) or Glen Research (Sterling, Va.)) to produce, for example, LC-RED 640-Phosphoramidite. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as fluorescein-CPG from BioGenex (San Ramon, Calif.)), or 3'-amino-CPG's that require coupling of a fluorescein-NHS-ester after oligonucleotide synthesis.

In one embodiment of the invention, the detecting step comprises exciting the sample at a wavelength absorbed by the donor fluorescent moiety and visualizing and/or measuring the wavelength emitted by the acceptor fluorescent moiety. The detecting step comprises quantitating the FRET. Fluorescent analysis can be carried out using, for example, a photon counting epifluorescent microscope system (containing the appropriate dichroic mirror and filters for monitoring fluorescent emission at the particular range), a photon counting photomultiplier system or a fluorometer. Excitation to initiate energy transfer can be carried out with an argon ion laser, a high intensity mercury (Hg) arc lamp, a fiber optic light source, or other high intensity light source appropriately filtered for excitation in the desired range.

Another subject of the invention relates to an alternative method of detecting the presence or absence of methicillin-resistant *S. aureus* (MRSA) in a sample, the method comprising:

(a) performing an amplifying step comprising contacting the sample with a set of MRSA primers to produce an amplification product if MRSA is present in the sample, (b) performing a hybridizing step comprising contacting the amplification product of step (a) with a MRSA probe, wherein the MRSA probe is labeled with a donor fluorescent moiety and with a corresponding acceptor fluorescent moiety; and (c) detecting the presence or absence of fluorescence resonance energy transfer (FRET) between the donor fluorescent moiety and the acceptor fluorescent moiety of the MRSA probe, wherein the absence of FRET is indicative of the presence of MRSA in the sample and wherein the presence of FRET is indicative of the absence of MRSA in the sample, wherein the method is capable of detecting each of Staphylococcal Chromosomal Cassettes (SCCmec) types I to V of MRSA.

A common format of FRET technology utilizes two hybridization probes, wherein each probe can be labeled with a different fluorescent moiety and are generally designed to hybridize in close proximity to each other in a target DNA molecule (e.g., an amplification product) (see above). However, an alternative FRET format utilizes a hydrolyzation probe (second method of the invention) to detect the presence or absence of an amplification product, and hence, the presence or absence of MRSA. This technology utilizes one single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hydrolyzation probe binds to the target DNA (i.e., the amplification product) and is degraded by the 5' to 3' exonuclease activity of a TAQ Polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems, Foster City, Calif.) uses hydrolyzation probe technology, and is suitable for performing the methods described herein for detecting MRSA. Information on PCR amplification and detection using an ABI PRISM® 770 system can be found at appliedbiosystems.com/products on the World Wide Web.

Examples of Suitable Hydrolyzation Probes are

```
                                        (SEQ ID NO: 87)
TP mec   5'- AAG TCG CTT TGC CCT TGG GTC AT -3'
1:
and (SEQ ID NO: 88)
TP mec   5'- TGC TCA ATT AAC ACA ACC CGC ATC A -3'.
2:
```

In another embodiment of the invention, the method may be further defined by one or more of the following features:
 a) the set of primers is as defined above in the context of the first method of the invention comprising or consisting of a primer specific for MRSA type RE2, a primer specific for MRSA type RE3 and a primer specific for MRSA type RE7,
 b) the probe comprises or consists of two fluorescent moieties, for example, as defined in above in the context of the first method of the invention, and a nucleic acid sequence of any of the SEQ ID NOS: 45 to 76, 96 or 97 or a functionally active variant thereof as defined in the context of the first method of the invention
 c) the amplifying step employs a polymerase enzyme having 5' to 3' exonuclease activity
 d) the donor and acceptor fluorescent moieties are within no more than 5 nucleotides of each other on the probe
 e) the probe comprises a nucleic acid sequence that permits secondary structure formation, wherein the secondary structure formation results in spatial proximity between the donor and acceptor fluorescent moiety
 f) the acceptor fluorescent moiety is a quencher.

Molecular beacons in conjunction with FRET also can be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Examples of Suitable Molecular Beacons are

```
                                        (SEQ ID NO: 89)
MB mec 1:
5'- GCC GCG CTG CTC AAT TAA CAC AAC CCG CGC GGC-3'
and (SEQ ID NO: 90)
MB mec 2:
5'- GCC GCG CAT GCG TTG GTT CAA TTC TGC GCG GC-3'.
```

It is noted that the details above related to using two probes apply analogously to the methods using one probe of the invention, with the exception that in the second method of the invention, only one probe labeled with a donor fluorescent moiety and with a corresponding acceptor fluorescent moiety is used.

Accordingly, as used herein, "fluorescence resonance energy transfer relationship" and similar terms refer to a "probe" labeled with a "donor fluorescent moiety" and an "acceptor fluorescent moiety" such that the "donor fluorescent label" can transfer resonance energy to the "acceptor fluorescent label" such that the "acceptor fluorescent label" produces a measurable fluorescence emission. If the "donor fluorescent label" and "acceptor fluorescent label" are spaced apart by too great a distance, then the "donor fluorescent label" cannot transfer resonance energy to the "acceptor fluorescent label" such that the "acceptor fluorescent label" emits measurable fluorescence, and hence the "donor fluorescent label" and "acceptor fluorescent label" are not in resonance energy transfer relationship. The acceptor fluorescent moiety can be a quencher absorbing the energy emitted by the donor fluorescent moiety.

The first (using (a) hybridization probe(s)) and second method (using (a) hydrolyzation probe(s) or (a) molecular beacon(s)) according to the invention may be performed in a format for the use in the LightCycler® instrument which is described in U.S. Pat. No. 6,174,670. This format comprises amplification and detection whereby the latter uses the detection of the fluorescence for the detection of the binding product between a pair of probes or a single probe and the target nucleic acid. These formats apply the FRET technology (see, for example, U.S. Pat. Nos. 4,996,143, 5,565,322, 5,849,489, and 6,162,603). As used herein, two probes, each containing a fluorescent label, or a single probe containing both fluorescent labels can hybridize to an amplification product at particular positions determined by the complementarity of the probes to the target nucleic acid. The fluorescent label may be a donor or acceptor fluorescent label. Upon hybridization of the probe(s) to the amplification product at the appropriate positions, a FRET signal is generated. The exemplified components as detailed above may be used (e.g., the detection devices, light sources, etc.)

In one embodiment of the invention, the amplifying step a) in the first method according to the invention comprises contacting the sample with the set of primers and optionally a suitable polymerase, usually by PCR, to produce an amplification product if MRSA nucleic acid is present in said sample, wherein said hybridizing step b) comprises contacting said sample with the pair of probes, wherein the members of said pair of probes hybridize to said amplification product within no more than five nucleotides of each other, wherein the first probe of said pair of probes is labeled with a donor fluorescent label and wherein the second probe of said pair of probes is labeled with a corresponding acceptor fluorescent label; and detecting the binding product between the MRSA nucleic acid and the pair of probes in step c) by detecting the presence or absence of FRET between said donor fluorescent label of said first probe and said acceptor fluorescent label of said second probe, wherein the presence of FRET is indicative of the presence of the target nucleic acid in the sample, and wherein the absence of FRET is indicative of the absence of the target nucleic acid in the sample.

In an alternative embodiment of the invention, the amplifying step a) in the second method according to the invention comprises contacting the sample with the set of primers and optionally a suitable polymerase to produce an amplification product if MRSA nucleic acid is present in said sample, wherein said hybridizing step b) comprises contacting said sample with the probe, wherein the probe is labeled with a donor fluorescent label and a corresponding acceptor fluorescent label, e.g. a quencher, and wherein the probe hybridizes to said amplification product; and detecting the binding product between the MRSA nucleic acid and the probe in step c) by detecting the presence or absence of FRET between said donor fluorescent label of the probe and the acceptor fluorescent label, wherein the presence or absence of FRET is indicative of the presence or absence of the target nucleic acid in the sample.

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in the present invention include oligonucleotides capable of acting as a point of initiation of nucleic acid synthesis within a MRSA nucleic acid sequence.

A primer can be purified from a restriction digest by conventional methods, or it can be produced synthetically. A primer is preferably single-stranded for maximum efficiency in amplification. The primer may be produced by chemical synthesis.

PCR assays can employ nucleic acid (DNA or RNA) template in general DNA. The template nucleic acid need not be purified; it may be a minor fraction of a complex mixture, such as MRSA toxin nucleic acid contained in human cells. DNA (or RNA) may be extracted from any sample such as body fluids or swabs by routine techniques such as those described in *Diagnostic Molecular Microbiology: Principles and Applications* (Persing et al. (eds), 1993, American Society for Microbiology, Washington D.C).

The oligonucleotide primers are combined with other PCR reagents under reaction conditions that induce primer extension. For example, chain extension reactions generally include 50 mM KCl, 10 mM Tris-HCl (pH 8.3), 1.5 mM $MgCl_2$, 0.001% (w/v) gelatin, 0.5-1.0 μg denatured template DNA, 50 pmoles of each oligonucleotide primer, 2.5 U of Taq polymerase, and 10% DMSO. The reactions usually contain 150 to 320 μM each of dATP, dCTP, dTTP, dGTP, or one or more analogs thereof. In certain circumstances, 300 to 640 μM dUTP can be substituted for dTTP in the reaction.

The newly synthesized strands form a double-stranded molecule that can be used in the succeeding steps of the reaction. The steps of strand separation, annealing, and elongation can be repeated as often as needed to produce the desired quantity of amplification products corresponding to the target MRSA nucleic acid molecule. The limiting factors in the reaction are the amounts of primers, thermostable enzyme, and nucleoside triphosphates present in the reaction. The amplification step and the hybridization step are preferably repeated at least once. For use in detection, the number of amplification and hybridization steps will depend, e.g., on the nature of the sample. If the sample is a complex mixture of nucleic acids, more amplification and hybridization steps may be required to amplify the target sequence sufficient for detection. Generally, the amplification and hybridization steps are repeated at least about 20 times, but may be repeated as many as 40, 60, or even 100 times. In a preferred embodiment of the invention, the presence of the FRET within 55, 45 or 35 cycles of amplification and hybridization is indicative of the presence of MRSA in the sample.

The polymerase chain reaction may comprise the steps of adding a thermostable polymerase, nucleotides and primers, whereby a primer can be a primer according to the invention, and the target nucleic acid to the sample and thermally cycling the sample between at least a denaturation temperature and an elongation temperature; exciting the sample with light at a wavelength absorbed by the donor fluorescent label and detecting fluorescent emission from the fluorescence energy transfer pair.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR provided the enzyme is replenished.

In another embodiment of the invention, a method for the detection of a MRSA nucleic acid comprises the steps of amplifying the nucleic acid by polymerase chain reaction in the presence of two nucleic acid probes that hybridize to adjacent regions of the nucleic acid, one of said probes being labeled with an acceptor fluorescent label and the other probe labeled with donor fluorescent label of a fluorescence energy transfer pair such that upon hybridization of the two probes with the target nucleic acid, the donor and acceptor fluorescent labels are within 25 nucleotides of one another, said polymerase chain reaction comprising the steps of adding a thermostable polymerase, nucleotides and primers, whereby the primers are as defined above, and the target nucleic acid to the sample and thermally cycling the sample between at least a denaturation temperature and an elongation temperature; exciting the sample with light at a wavelength absorbed by the donor label and monitoring temperature dependent fluorescence from the fluorescence energy transfer pair.

In another alternative embodiment of the invention, a method for the detection of a MRSA nucleic acid comprises the steps of amplifying the nucleic acid by polymerase chain reaction in the presence of one nucleic acid probe being labeled with an acceptor fluorescent label, e.g., a quencher, and a donor fluorescent label of a fluorescence energy transfer pair, hybridizing the probe with the target nucleic acid, said polymerase chain reaction comprising the steps of adding a polymerase optionally having 5' to 3' exonuclease activity, nucleotides, and primers, whereby the primers are as defined above, and the target nucleic acid to the sample and thermally cycling the sample between at least a denaturation temperature and an elongation temperature; exciting the sample with light at a wavelength absorbed by the donor label and monitoring the fluorescence from the fluorescence energy transfer pair of labels.

For the above-described methods, the nucleic acids can be present in double-stranded or single-stranded form. If the nucleic acid template is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 0 sec to 4 min.

In one embodiment of the invention, the detecting step is performed after each step of amplification and hybridization and/or in real-time. A detailed description of real-time and on-line monitoring of PCR can be found at biochem.roche.com/lightcycler on the World Wide Web. The following patent applications describe real-time PCR as used in the LightCycler® technology: WO 97/46707, WO 97/46714 and WO 97/46712. The LightCycler® instrument is a rapid thermal cycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the LightCycler® thermal chamber. Addition of selected fluorescent dyes to the reaction components allows the PCR to be monitored in real time and on-line. Furthermore, the cuvettes serve as an optical element for signal collection (similar to glass fiber optics), concentrating the signal at the tip of the cuvette. The effect is efficient illumination and fluorescent monitoring of microvolume samples. Exemplary PCR protocols are described in Example 3.

The LightCycler® carousel that houses the cuvettes can be removed from the instrument. Therefore, samples can be loaded outside of the instrument (in a PCR Clean Room, for example). In addition, this feature allows for the sample carousel to be easily cleaned and sterilized. The fluorometer, as part of the LightCycler® apparatus, houses the light source. The emitted light is filtered and focused by an epi-illumination lens onto the top of the cuvette. Fluorescent light emitted from the sample is then focused by the same lens, passed through a dichroic mirror, filtered appropriately, and focused onto data-collecting photohybrids. The optical unit currently available in the LightCycler® instrument (Roche Diagnostics GmBH, Catalog No. 03531414001) includes six band-pass filters (530 nm, Hex excitation, 610 nm, 640 nm, 670 nm, and 705 nm), providing four-color detection and several fluorescence acquisition options. Data collection options include once per cycling step monitoring, fully continuous single-sample acquisition for melting curve analysis, continuous sampling (in which sampling frequency is dependent on sample number) and/or stepwise measurement of all samples after defined temperature interval.

The LightCycler® can be operated using a PC workstation and can utilize a Windows operating system, e.g., Windows XP, Windows NT or Windows 2000. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

In still another embodiment of the invention, the method further comprises determining the melting temperature between one of the two probes and the amplification product of step (a), wherein the melting temperature confirms the presence or the absence of MRSA. Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition and its length. Thus, DNA molecules rich in G and C nucleotides and/or longer in nucleotides have a higher Tm than those having an abundance of A and T nucleotides and/or shorter in nucleotides. By detecting the temperature at which signal is lost, the melting temperature of probes can be determined. Similarly, by detecting the temperature at which signal is generated, the annealing temperature of probes can be determined. The melting temperature(s) of the MRSA probes from the respective amplification product can confirm the presence of MRSA in the sample.

In still another embodiment of the invention, the method further comprises preventing amplification of a contaminant nucleic acid, particularly comprising performing the amplification step (a) in the presence of uracil. Such a method generally includes comprising treating the sample with uracil-DNA glycosylase prior to a first amplifying step. For example, an enzymatic method utilizing uracil-DNA glycosylase is described in U.S. Pat. Nos. 5,035,996, 5,683,896 and 5,945,313 to reduce or eliminate contamination between one thermocycler run and the next. In addition, standard laboratory containment practices and procedures are desirable when performing methods of the invention. Containment practices and procedures include, but are not limited to, separate work areas for different steps of a method, containment hoods, barrier filter pipette tips and dedicated air displacement pipettes. Consistent containment practices and procedures by personnel are desirable for accuracy in a diagnostic laboratory handling clinical samples.

Before the nucleic acids of the sample may be analyzed in one of the above-mentioned assays, they might have to be isolated or purified from (biological) samples containing complex mixtures of different components. Often, for the first steps, processes are used which allow the enrichment of the nucleic acids.

In a preferred embodiment of the methods of the invention, the sample may be used as crude lysate, which may be prepared as follows:

The sample, e.g. a swab, may be transferred to a suitable buffer and may optionally be treated in order to inactivate bacteria. To release the contents of cells, they may be treated with enzymes or with chemicals to dissolve, degrade or denature the cellular walls. This process is commonly referred to as lysis or mechanical lysis. The resulting solution containing such lysed material is referred to as lysate. The lysate may be purified, e.g., by spinning the lysate and discarding the pellet (debris). The supernatant may be used directly as sample in an amplification reaction.

For example, the S.E.T.S. kit (Roche Diagnostics Corporation, Catalog No. 03753158001) may be use in order to prepare a crude lysate. The method can be exemplarily described as follows: the sample, e.g., a swab, is broken of the handle and the swab tip is inserted into inner S.E.T.S. tubes (e.g. 0.5 ml tube containing a hole in the bottom and fitting into outer S.E.T.S. tubes, when closed). Tubes are places in outer S.E.T.S. tubes containing silica beads and neutralization buffer (NB). NB neutralizes the transportation medium derived from the swabbing device. Adhering material from the swab is removed from the swab tip and transferred into the outer S.E.T.S. tube by gravitation force (centrifugation). The S.E.T.S. tube is closed and heated to 95° C. for heat inactivation of bacteria. Cells are disrupted by mechanical force in a shaking device e.g. the MagNALyser® Instrument. Debris is collected in the bottom of the tube by a short spin and the supernatant is used directly as sample in an amplification reaction. The method is described into more detail in Uhl et al., 2005, *J Clin Microbiol.* 8:4046-51.

A problem encountered during lysis is that other enzymes, e.g., deoxyribonucleases or ribonucleases, come into contact with the component of interest during lysis and degrade the nucleic acids. These degrading enzymes may also be present outside the cells or may have been spatially separated in different cellular compartments before the lysis and now come into contact with the component of interest. Other components released during this process may be, e.g., endotoxins, belonging to the family of lipopolysaccharides, which are toxic to cells and can cause problems for products intended to be used in human or animal therapy.

There are a variety of means to tackle this problem mentioned-above. It is common to use chaotropic agents as, e.g., guanidinium thiocyanate or anionic, cationic, zwitterionic or non-ionic detergents when nucleic acids are intended to be set free. It is also an advantage to use proteases that rapidly degrade these enzymes or unwanted proteins. However, those substances or enzymes can interfere with reagents or components in subsequent steps.

Enzymes that can be advantageously used in such lysis or sample preparation processes mentioned above are enzymes which cleave the amide linkages in protein substrates and which are classified as proteases, or (interchangeably) peptidases (see Walsh, 1979, *Enzymatic Reaction Mechanisms*, W.H. Freeman & Co., San Francisco, Chapter 3). Proteases that have been used in the prior art are, e.g., alkaline proteases (WO 98/04730) or acid proteases (U.S. Pat. No. 5,386,024). A protease that is widely used in the prior art for sample preparation for the isolation of nucleic acids is proteinase K from *Tritirachium album* (see e.g. Sambrook et al., *Molecular Cloning: A Laboratory Manual, Cold Spring Harbor Laboratory Press, Cold Spring Harbor, N.Y.,* 1989) which is active around neutral pH and belongs to a family of proteases known to the person skilled in the art as subtilisins.

In the steps of the sample preparation that follow the lysis step, the component of interest can be further enriched. If the non-proteinaceous components of interest are, e.g., nucleic acids, they are normally extracted from the complex lysis mixtures before they are used in a probe-based assay.

There are several methods available for the extraction of nucleic acids:
sequence-dependent or biospecific methods such as e.g.:
affinity chromatography
hybridization to immobilized probes
sequence-independent or physico-chemical methods such as e.g.:
liquid-liquid extraction with, e.g., phenol-chloroform
precipitation with, e.g., pure ethanol
extraction with filter paper
extraction with micelle-forming agents as cetyl-trimethyl-ammonium-bromide
binding to immobilised, intercalating dyes, e.g., acridine derivatives
adsorption to silica gel or diatomic earths
adsorption to magnetic glass particles (MGP) or organo silane particles under chaotropic conditions Another method of extracting nucleic acids is the adsorption of nucleic acids to a glass or other surface. Many procedures for isolating nucleic acids from their natural environment have been proposed in recent years by the use of their binding behavior to glass or other surfaces. If unmodified nucleic acids are the target, a direct binding of the nucleic acids to a material with a silica surface is preferred because, among other reasons, the nucleic acids do not have to be modified and even native nucleic acids can be bound. These processes are described in detail by various documents. In Vogelstein et al., 1979, *Proc. Natl. Acad. U.S.A.* 76: 615-619, for instance, a procedure for binding nucleic acids from agarose gels in the presence of sodium iodide to ground flint glass is proposed. The purification of plasmid DNA from bacteria on glass dust in the presence of sodium perchlorate is described in Marko et al., 1982, *Anal. Biochem.* 121:382-387. In DE 37 34 442, the isolation of single-stranded M13 phage DNA on glass fiber filters by precipitating phage particles using acetic acid and lysis of the phage particles with perchlorate is described. The nucleic acids bound to the glass fiber filters are washed and then eluted with a methanol-containing Tris/EDTA buffer. A similar procedure for purifying DNA from lambda phages is described in Jakobi et al., 1988, *Anal. Biochem.* 175:196-201. The procedure entails the selective binding of nucleic acids to glass surfaces in chaotropic salt solutions and separating the nucleic acids from contaminants such as agarose, proteins or cell residue. To separate the glass particles from the contaminants, the particles may be either centrifuged or fluids are drawn through glass fiber filters. This is a limiting step, however, that prevents the procedure from being used to process large quantities of samples.

The use of magnetic particles to immobilize nucleic acids after precipitation by adding salt and ethanol is more advantageous and described, e.g., in Alderton et al., 1992, *Anal. Biochem.* 201:166-169 and PCT GB 91/00212. In this procedure, the nucleic acids are agglutinated along with the magnetic particles. The agglutinate is separated from the original solvent by applying a magnetic field and performing a wash step. After one wash step, the nucleic acids are dissolved in a Tris buffer. This procedure has a disadvantage, however, in that the precipitation is not selective for nucleic acids. Rather, a variety of solid and dissolved substances are agglutinated as well. As a result, this procedure can not be used to remove significant quantities of any inhibitors of specific enzymatic reactions that may be present. Magnetic, porous glass is also available on the market that contains magnetic particles in a porous, particular glass matrix and is covered with a layer containing streptavidin. This product can be used to isolate biological materials, e.g., proteins or nucleic acids, if they are modified in a complex preparation step so that they bind covalently to biotin. Magnetizable particular adsorbents proved to be very efficient and suitable for automatic sample preparation. Ferrimagnetic and ferromagnetic as well as superparamagnetic pigments are used for this purpose. In one embodiment, the methods of using magnetic glass particles disclosed in WO 01/37291 are used.

After the purification or isolation of the nucleic acids including the target nucleic acid from their natural surroundings, the target nucleic acid (i.e., the MRSA-specific nucleic acid) may be detected.

Within each thermocycler run, control samples can be cycled as well. Accordingly, in a further embodiment of the invention, the method of the invention includes a control sample, wherein the control sample comprises MRSA nucleic acid molecule. Control nucleic acid template can be amplified from a positive control (reagent control) sample using, for example, control primers and control probes. Positive control samples can also be used to amplify, for example, a plasmid construct containing MRSA nucleic acid molecules. Such a plasmid control can be amplified internally (e.g., within each biological sample) (internal control) or in separate samples run side-by-side with the patients' samples. Each thermocycler run also should include a negative control that, for example, lacks MRSA nucleic acid. Such controls are indicators of the success or failure of the amplification, hybridization, and/or FRET reaction. Therefore, control reactions can readily determine, for example, the ability of primers to anneal with sequence-specificity and to initiate elongation, as well as the ability of probes to hybridize with sequence-specificity and for FRET to occur.

One representative control concept comprises a positive control (detecting a known MRSA DNA), a reagent control (detecting a plasmid comprising the MRSA target sequence) and an internal control (detecting a plasmid comprising the MRSA target sequence, wherein the probe binding site, e.g. that for the MRSA sensor probe, has been substituted by another sequence which does not bind the MRSA sensor probe but which is recognized by the internal control sensor probe; alternatively, the binding sites for both probes may be exchanged). The internal control may be part of each of the reactions, i.e., the positive control, reagent control, negative control, and each sample.

An example of a suitable probe for internal control is:

```
MRSA IC 4:
5'- CCA GCA GAA TGC CAA CCA -3',    (SEQ ID NO: 91)
e.g., 5' labelled with LC-Red 670
or MRSA direct IC:
5'-CCA GCA GAA TGC CAG CCA AT-3',   (SEQ ID NO: 98)
e.g., 5' labelled with LC-Red 670.
```

The sample to be analyzed may be any sample. However, the sample will in general be a biological sample, preferably a sample from a human subject. Representative biological samples that can be used in practicing the methods of the invention include swabs or body fluids such as a sample selected from the group consisting of a swab of an infected wound, a skin swab, a nasal swab, a throat swab, a groin swab, an axilla swab, a swab from site of an invasive device, a swab from site of possible infection, a blood sample, a urine sample and a perineum swab. Biological sample collection and storage methods are known to those of skill in the art. Biological samples can be processed (e.g., by standard nucleic acid extraction methods and/or using commercial kits) to release MRSA nucleic acid, or the biological sample can be contacted directly with the PCR reaction components and the appropriate oligonucleotides. Inadequate specimen collection, transportation delays, inappropriate transportation conditions, or use of certain collection swabs (e.g., calcium alginate or aluminum shaft) are all conditions that can affect the success and/or accuracy of the test result.

A further subject of the invention relates to a primer, a set of primers, a probe and/or a pair of probes as defined in any of the above embodiment of the invention.

Still a further subject of the present invention relates to a kit comprising:

(a) a set of primers as defined in any of the above embodiment of the invention and as set forth in SEQ ID NO:1-32 or 92-94;
(b) a pair of probes or a probe as defined in any of the above embodiment of the invention, particularly a set of primers comprising or consisting of a primer specific for MRSA type RE2, a primer specific for MRSA type RE3 and a primer specific for MRSA type RE7; and
(c) a donor fluorescent moiety and a corresponding fluorescent moiety labeling the probe(s), wherein the kit is capable of detecting each of Staphylococcal Chromosomal Cassettes (SCCmec) types I to V of MRSA.

The set of primers, probe and/or pair of probes may be as described for the above embodiments or suitable for any of the methods of the invention described above. Additionally, the kit may comprise a package label or package insert having instructions thereon for using the pair of MRSA primers and the pair of MRSA probes to detect the presence or absence of in a sample. Further optional components of the kit of the invention are at least one suitable enzyme such as uracil-DNA-glycosylase and/or a DNA polymerase, and/or a suitable buffer. The kit may also contain a template-dependent polymerase having 3' to 5' exonucleolytic activity such as the Taq Polymerase, nucleotides and oligonucleotides. In another embodiment of the invention, a kit is provided comprising a template dependent DNA polymerase, nucleotides and an oligonucleotide or a pair of primers according to the invention.

Such kits known in the art further comprise plasticware that can be used during the amplification procedure as, e.g., microtitre plates in the 96 or 384 well format or just ordinary reaction tubes manufactured, e.g., by Eppendorf (Hamburg, Germany) and all other reagents for carrying out the method according to the invention.

In another embodiment of the invention, the kit contains further reagents for isolating the nucleic acid. Therefore, the kit can additionally contain a material with an affinity to nucleic acids such as a material with a silica surface (e.g., a glass, e.g., a composition comprising magnetic glass particles as described in WO 96/41811 or WO 01/37291). The kit can further or additionally comprise a lysis buffer containing e.g. chaotropic agents, detergents or alcohols or mixtures thereof which allows the lysis of cells and separately a protease, e.g. proteinase K, for the digestions of unwanted proteins. These components of the kit according to the invention may be provided separately in tubes or storage containers. Depending on the nature of the components, these may be even provided in a single tube or storage container. The kit may further or additionally comprise a washing solution which is suitable for the washing step of the magnetic glass particles when DNA or RNA is bound thereto. This washing solution may contain ethanol and/or chaotropic agents in a buffered solution or solutions with an acidic pH without ethanol and/or chaotropic agents as described above. Often the washing solution or other solutions are provided as stock solutions which have to be diluted before use. The kit may further or additionally comprise an eluent or elution buffer, i.e., a solution or a buffer (e.g., 10 mM Tris, 1 mM EDTA, pH 8.0) or pure water to elute the DNA or RNA bound to the magnetic glass particles. Further, additional reagents or buffered solutions may be present which can be used for the purification process of a nucleic acid, i.e., DNA or RNA.

In one embodiment of the invention, the kit contains inner, outer S.E.T.S. tubes and/or the neutralization buffer as sample prep reagents. The method of the invention can be carried out without purification of the samples by preparing crude lysates, e.g., as detailed above. Accordingly, the kit may be adapted to this method in that means for further isolation or purification of nucleic acids are not included into the kit.

Another embodiment of the present invention is to use the method or the kit of the present invention in automatable methods as, e.g., described in WO 99/16781. Automatable method means that the steps of the method are suitable to be carried out with an apparatus or machine capable of operating with little or no external control or influence by a human being. Automated method means that the steps of the automatable method are carried out with an apparatus or machine capable of operating with little or no external control or influence by a human being. Only the preparation steps for the method may have to be done by hand, e.g., the storage containers have to filled up and put into place, the choice of the samples has to be done by a human being and further steps known to the expert in the field, e.g., the operation of the controlling computer. The apparatus or machine may, e.g., add automatically liquids, mix the samples or carry out incubation steps at specific temperatures. Typically, such a machine or apparatus is a robot controlled by a computer which carries out a program in which the single steps and commands are specified. Automated methods are those which are carried out in a high-throughput format which means that the methods and the used machine or apparatus are optimized for a high-throughput of samples in a short time. In another embodiment of the invention, the methods or the kits according to the present invention are used in semi-automated process which means that some reaction steps may have to be done manually. In another embodiment of the invention, a suspension containing magnetic particles according to the present invention is taken from a storage container and partial volumes are added to different reaction vessels. Reaction vessels may be reaction tubes made from plastics eventually in microtitre plate format contain 96 or 384 or more wells where a reaction can be carried out. However, these vessels may be made from other material, e.g., from steel.

In embodiments of the invention, the kit according to the invention is used for research, bioanalytics or diagnostics. In alternative embodiments according to the invention, the kit or the method of the invention is used in a high-throughput format, i.e., in an automated method which allows the analysis of a high number of different samples in a very short time.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. Additionally, it is understood that the present invention is not limited by the configuration of one or more commercially available instruments, particularly those described herein.

FIGURES

FIG. 1 shows amplicon sequences for MRSA, particularly RE2, RE3 and RE7 (each including the beginning of orfx (CC)) as well as orfx.

——— primer
·········· first probe (anchor probe)
----- second probe (sensor probe) indicates a mismatch FIG. 2 shows the sequence of RE2 alignment from 93 different MRSA strains. Point mutations including the number of mutations and the kind of alterations are given. A 102 bp duplication present in SCCmec type I is identified by _____. The transition from SCCmec to the SA portion of the sequence is identified by CC.

FIG. 3 shows amplification curves (FIG. 3A) and melting curves (FIG. 3B) for RE2 detection. In analytical experiments, a dynamic range of 5 log steps and a sensitivity in the range of 10 genomic copies proved fulfillment of requirements for diagnostic use. This experiment proves functionality of the assay.

Figure 4B:
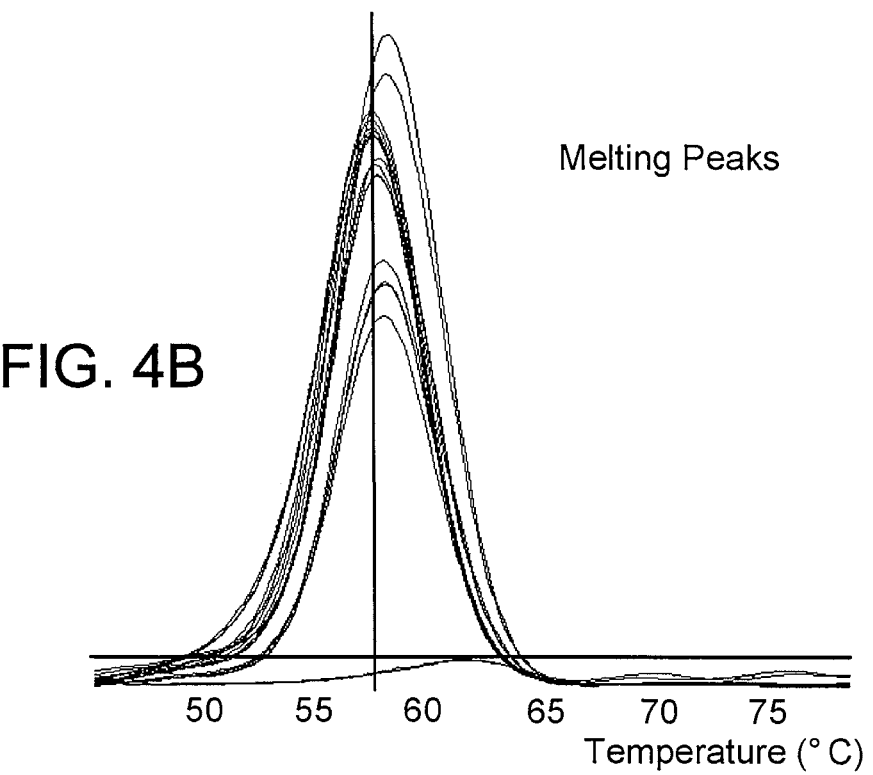

FIG. 4 shows amplification curves (FIG. 4A) and melting curves (FIG. 4B) for RE3 detection. In analytical experiments, a dynamic range of 5 log steps and a sensitivity in the range of 10 genomic copies proved fulfillment of requirements for diagnostic use. This experiment proves functionality of the assay.

Figure 5A:
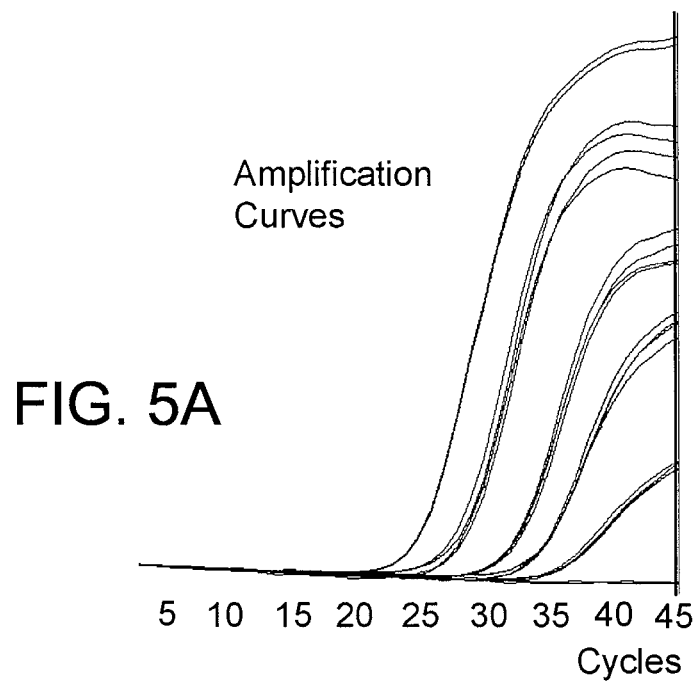
Figure 5B:
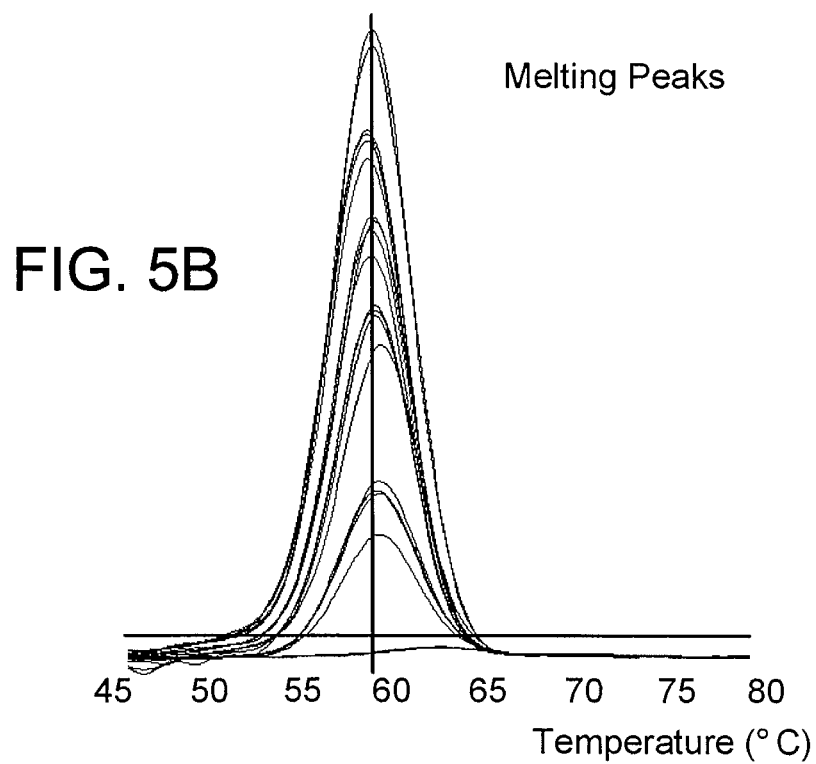

FIG. 5 shows amplification curves (FIG. 5A) and melting curves (FIG. 5B) for RE7 detection. In analytical experiments, a dynamic range of 5 log steps and a sensitivity in the range of 10 genomic copies proved fulfillment of requirements for diagnostic use. This experiment proves functionality of the assay.

EXAMPLES

Example 1

Diagnostic In Vitro Test for MRSA

The LightCycler® MRSA direct test is a qualitative in vitro diagnostic test for the direct detection of methicillin resistant *Staphylococcus aureus* (MRSA) to aid in the prevention and control of MRSA colonization in e.g. healthcare settings. The test performed on the LightCycler® 2.0 Instrument with specimens from patients suspected for colonization, utilized swab extraction and mechanical lysis for specimen preparation followed by polymerase chain reaction (PCR) for the amplification of MRSA DNA and fluorogenic target specific hybridization probes for the detection of the amplified DNA.

Instrument Requirements: For this assay, the LightCycler® 2.0 was used.

Reagent Requirements: The assay consisted of the sample prep reagents and amplification reagents. Sample preparation was carried out by extraction of bacteria from swabs and a subsequent lysis step. Lysis can be done either enzymatically or mechanically. For *S. aureus*, mechanical lysis showed good results in the past. In addition, mechanical lysis can be done irrespective of the bacteria or bacterial phenotype present in the sample. Therefore, mechanical lysis was the favored method. For further processing of the lysate, two options are possible.

1. Sample lysis with subsequent DNA extraction
2. Sample lysis and use of crude extracts Since time to result was important and lysis alone is fast, no DNA purification was done and only a crude lysate was generated and directly used for PCR.

The assay used amplification by PCR and detection by FRET probes. Controls for amplification and internal controls were included, in order to control amplification and hybridization. Detection was either by amplification curve or melting curve analysis.

Software Requirements The software SW 4.05 was used for data analysis of the MRSA direct test. For data analysis, two possible algorithms may be used.

When amplification curves were used (qualitative detection module), data output was achieved by the LightCycler SW without further manual steps. Programming, the control concept and the display of the outcome was steered via a macro. For this solution, data output relied on the SW intrinsic algorithm. The data outcome was not controlled via an expert analysis.

Melting curve analysis required a manual analysis step be performed. The advantage was a slightly better specificity.

Workflow description: The workflow for the MRSA direct test encompassed:
1. Swab extraction using the Neutralization buffer, inner and outer S.E.T.S. tubes.
2. Lysis of the bacteria including addition of the internal control (IC) via the neutralization buffer (heat and mechanical disrupt).
3. Transfer of the crude lysate (specimen extract) to the Reaction Mix (RM). The RM consisted of the primer and probes, the FastStart enzyme (Taq polymerase), UNG (uracil-N-glycosilase) and buffer.
4. Amplification and detection using specific primer and probes (PCR).
5. Data analysis in two steps; first, validation of the experiment via the respective control, and second, identification of the presence or absence of the target analyte.

Example 2

Design of Primers and Probes

The primer and probes were designed so that the reverse primer and the pair of probes (detection probes) are located in the *S. aureus* portion of the target region. Therefore, this element remained the same for all RE types. RE types describe the sequence variations of the right extremity junction of the SCC mec transposon. The RE2 amplicon representing the majority of all RE types has been evaluated by sequencing 93 unrelated specimens (FIG. 2). For this predominant RE type (representing SCCmec type I, I, III (some) and some IV), primers and probes have been designed (see Table 1). This represents the core assay. Further primers in order to cover SCC types I to V were added when appropriate (see Table 1). For primer and probe design, LightCycler® Probe Design Software 2.0 was used. Variants of these primers and probes were designed in order to optimize signal output (see Table 1).

TABLE 1

Primer and Probe design for SCCmec RE2, RE3 and RE7 detection

| Primer/<br>Probe ID | Label | Sequence (shown without label) | (SEQ ID NO:) |
|---|---|---|---|
| Primers for detection of RE2 | | | |
| AR mec 1 fwd | none | 5'- GCA ATT CAC ATA AAC CTC ATA TGT TC -3' | (1) |
| AR mec 2 fwd | none | 5'- ACC TCA TAT GTT CTG ATA CAT TCA -3' | (2) |
| AR mec 3 fwd | none | 5'- GCA ATT CAC ATA AAC CTC ATA T -3' | (3) |
| AR mec 4 fwd | none | 5'- CAT AAC AGC AAT TCA CAT AAA CCT C -3' | (4) |
| AR mec 5 fwd | none | 5'- TAA CAG CAA TTC ACA TAA ACC T -3' | (5) |
| AR mec 6 fwd | none | 5'- CGC TAT TAT TTA CTT GAA ATG AAA GAC -3' | (6) |
| AR mec 7 fwd | none | 5'- CTT GAA ATG AAA GAC TGC GGA -3' | (7) |
| AR mec 8 fwd | none | 5'- TTG CTT CAC TAT AAG TAT TCA GTA TAA AGA -3' | (8) |
| AR mec 9 fwd | none | 5'- ATT TAC TTG AAA TGA AAG ACT GCG -3' | (9) |
| AR mec 10 fwd | none | 5'- AAA GAA TAT TTC GCT ATT ATT TAC TTG AA -3' | (10) |
| AR mec 11 fwd | none | 5'- TCA GTA TAA AGA ATA TTT CGC TAT TAT TT -3' | (11) |
| AR mec 12 fwd | none | 5'- TGA AAT GAA AGA CTG CGG AG -3' | (12) |
| JU1 fwd | none | 5'- AAC CTC ATA TGT TCT GAT ACA TTC AAA -3' | (13) |
| JU2 fwd | none | 5'- TAT GTC AAA AAT CAT GAA CCT CAT TAC T -3' | (14) |
| JU3 fwd | none | 5'- CAT AAC AGC AAT TCA CAT AAA CCT C -3' | (15) |
| JU4 fwd | none | 5'- GAC TGC GGA GGC TAA CT -3' | (16) |
| JU5 fwd | none | 5'- ATC CCT TTA TGA AGC GGC -3' | (17) |
| MRSA direct RE2 | | | |
| fwd | none | 5'-TGA AAT GAA AGA CTG CGG AT-3' | (92) |
| Primers for detection of RE3 | | | |
| AR mecA 3/1 | none | 5'- GCA AGG TAT AAT CCA ATA TTT CAT ATA TGT -3' | (18) |
| AR mecA 3/2 | none | 5'- AGT TCC ATA ATC AAT ATA ATT TGT ACA GT -3' | (19) |
| AR mecA 3/3 | none | 5'- ACA TCG TAT GAT ATT GCA AGG TA -3' | (20) |
| AR mecA 3/4 | none | 5'- CTT TCA TTC TTT CTT GAT TCC ATT AG -3' | (21) |
| AR mecA 3/5 | none | 5'- CAC TCT ATA AAC ATC GTA TGA TAT TGC -3' | (22) |
| AR mecA 3/6 | none | 5'- TTC TTA ATT TAA TTG TAG TTC CAT AAT CAA -3' | (23) |
| AR mecA 3/7 | none | 5'- AAT TAT ACA CAA CCT AAT TTT TAG TTT TAT -3' | (24) |
| AR mecA 3/8 | none | 5'- AAT TTT AGT TTA TTA TGA TAC GCT TC -3' | (25) |
| AR mecA 3/9 | none | 5'- ACA CAA CCT AAT TTT TAG TTT TAT TTA TGA -3' | (26) |
| AR mecA 3/10 | none | 5'- TTT ATT AAA CAC TCT ATA AAC ATC GTA TGA -3' | (27) |
| AR mecA 3/13 | none | 5'- CCA CAT CTC ATT AAA TTT TTA AAT TAT ACA C -3' | (28) |
| MRSA direct RE3 | | | |
| fwd | none | 5'- CCA CAT CTC ATT AAA TTT TTA AAT TAT ACA C -3' | (93) |

TABLE 1-continued

Primer and Probe design for SCCmec RE2, RE3 and RE7 detection

| Primer/Probe ID | Label | Sequence (shown without label) | (SEQ ID NO:) |
|---|---|---|---|
| Primers for detection of RE7 | | | |
| AR mec 5/1 | none | 5'- ATA TTA TAC ACA ATC CGT TTT TTA GTT TTA -3' | (29) |
| AR mec 5/2 | none | 5'- ACA CAA TCC GTT TTT TAG TTT TAT TTA TG -3' | (30) |
| AR mec 5/3 | none | 5'- TTC TAA TTT ATT TAA CAT AAA ATC AAT CCT -3' | (31) |
| AR mec 5/16 | none | 5'- CAA TCC TTT TTA TAT TTA AAA TAT ATT ATA CAC -3' | (32) |
| MRSA direct RE7 | | | |
| fwd | none | 5'- CAA TCC TTT TTA TAT TTA AAA TAT ATT ATA CAC -3' | (94) |
| Primers specific for MRSA/SSRA | | | |
| AR mec 1 rev | none | 5'- AGG AAA GAT GCT ATC TTC CGA -3' | (33) |
| AR mec 2 rev | none | 5'- GAA AGA TGC TAT CTT CCG AAG -3' | (34) |
| AR mec 3 rev | none | 5'- GAT GCT ATC TTC CGA AGG -3' | (35) |
| AR mec 4 rev | none | 5'- GTC ATT ACA TTA GAA ATA CAA GGA AAG AT -3' | (36) |
| AR mec 5 rev | none | 5'- GCC AAC GAA TAC TAG CC -3' | (37) |
| AR mec 6-2 rev | none | 5'- ACG AAT ACT AGC CAA AAT TAA ACC -3' | (38) |
| AR mec 7 rev | none | 5'- CAC AAT CCA CAG TCA TTA CAT TAG A -3' | (39) |
| JU1 rev | none | 5'- CAA GGA AAG ATG CTA TCT TCC G -3' | (40) |
| JU2 rev | none | 5'- AGT CAT TAC ATT AGA AAT ACA AGG AAA GA -3' | (41) |
| JU3 rev | none | 5'- AGGAAAGATGCTATCTTCCGA -3' | (42) |
| JU4 rev | none | 5'- AGG AAA GAT GCT ATC TTC CGA -3' | (43) |
| JU5 rev | none | 5'- ACA ATC CAC AGT CAT TAC ATT AGA A -3' | (44) |
| MRSA direct rev | none | 5'- CAA GGA AAG ATG CTA TCT TCC G -3' | (95) |
| Probes specific for orfX | | | |
| AR mec Fluo 1 | Fluos | 5'- AAG TCG CTT TGC CTT GGG TCA -3' | (45) |
| AR mec Fluo 2 | Fluos | 5'- TAC AAA GTC GCT TTG CCT TGG GGT CA -3' | (46) |
| AR mec Fluo 3 | Fluos | 5'- GGC CGT TTG ATC CGC CAA T -3' | (47) |
| AR mec Fluo 4 | Fluos | 5'- AAG TCG CTT TGC CCT TGG GTA -3' | (48) |
| AR mec Fluo 4-2 | Fluos | 5'- AAG TCG CTT TGC CCT TGG GT -3' | (49) |
| AR mec Fluo 4-3 | Fluos | 5'- AAG TCG CTT TGC CCT TGG GTC A -3' | (50) |
| AR mec Fluo 4-GV | Fluos | 5'- AAG TCG CTT TGC CCT TGG G -3' | (51) |
| AR mec Fluo 4k | Fluos | 5'- CAA GAA TTG AAC CAA CGC AT -3' | (52) |
| AR mec Fluo 5 | Fluos | 5'- CAA TGA CGA ATA CAT AGT CGC TTT GCC CTT -3' | (53) |
| AR mec Fluo 6 | Fluos | 5'- CGT TTG ATC CGC CAA TGA CGA -3' | (54) |
| AR mec Fluo 7 | Fluos | 5'- GCC AAT CCT TCG AAA GAT AGC A -3' | (55) |
| AR mec Fluo UR | Fluos | 5'- ATT AAC ACA ACC CGC ATC -3' | (56) |
| JU1 probe 1 | Fluos | 5'- GTC GCT TTG CCC TTG GGT C -3' | (57) |
| JU2 probe 1 | Fluos | 5'- TCG CTT TGC CCT TGG GTC AT -3' | (58) |
| JU3 probe 1 | Fluos | 5'- GGC CGT TTG ATC CGC CAA T -3' | (59) |
| JU4 probe 1 | Fluos | 5'- GTC CTT GTG CAG GCC GTT GA T -3' | (60) |
| JU5 probe 1 | Fluos | 5'- CTT GGG TCA TGC GTT GGT TCA ATT -3' | (61) |
| MRSA direct Fluos | Fluos | 5'- AAG TCG CTT TGC CCT TGG G -3' | (96) |
| AR mec 640 3 | LC Red 640 | 5'- CGA ATA CAA AGT CGC TTT GCC CTT GGG -3' | (62) |
| AR mec 640 4 | LC Red 640 | 5'- ATG CGT TGG TTC AAT TCT TG -3' | (63) |
| AR mec 610 4-3 | LC Red 610 | 5'- GCG TTG GTT CAA TTC TTG GG -3' | (64) |
| AR mec 640 4k | LC Red 640 | 5'- ACC CAA GGG CAA AGC GAC TT -3' | (65) |
| AR mec 640 5 | LC Red 640 | 5'- GGT AAT GCG TTG GTT CAA TTC TTG -3' | (66) |
| AR mec 640 6 | LC Red 640 | 5'- ACA AAG TCG CTA TGC CCT GGG TCA -3' | (67) |
| AR mec 640 7 | LC Red 640 | 5'- CTT TCC TTG TAT TTC TAA TGT AAT GAC TG -3' | (68) |
| AR mec 640 UR | LC Red 640 | 5'- TTG ATG TGG GAA TGT CAT TTT GCT GAA -3' | (69) |
| JU1 probe 2 | LC Red 640 | 5'- GCG TTG GTT CAA TTC TTG GGC CAA T -3' | (70) |

TABLE 1-continued

Primer and Probe design for SCCmec RE2, RE3 and RE7 detection

| Primer/Probe ID | Label | Sequence (shown without label) | (SEQ ID NO:) |
|---|---|---|---|
| JU2 probe 2 | LC Red 640 | 5'- GTT GGT TCA ATT CTT GGG CCA ATC TTC CG -3' | (71) |
| JU3 probe 2 | LC Red 640 | 5'- CGA ATA CAA AGT CGC TTT GCC CTT GG -3' | (72) |
| JU4 probe2 | LC Red 640 | 5'- GCC AAT GAC GAA TAC AAA GTC GCT TTG CC -3' | (73) |
| JU5 probe2 | LC Red 640 | 5'- TGG GCC AAT CCT TCG GAA GAT AGC A -3' | (74) |
| AR mec 610 4-MM2 | LC Red 610 | 5'- ATG CGT TGG TTC GAT TCT TG -3' | (75) |
| AR mec 610 4-MM2-GV | LC Red 610 | 5'- CAT GCG TTG GTT CGA TTC TTG -3' | (76) |
| MRSA direct Red610 | LC Red 610 | 5'- CAT GCG TTG GTT CGA TTC TTG -3' | (97) |

Example 3

Analysis of Particular Primers and Probes

For RE2, RE3 and RE7, single tests using the same probes and the same reverse primer but different forward primers were established (see Table 1). These single tests were analyzed for the dynamic range from about $10^6$ genomic copies/PCR to 10 copies/PCR in tenfold dilutions (FIGS. 3 to 5). For data analysis, the qualitative detection module and manual Tm calling were employed.

Reagent Concentrations:
forward primers: 0.2-0.5 µM
reverse primer: 0.3-0.5 µM
probes: 0.1-0.4 µM
$MgCl_2$: 3.0-4.5 mM (final concentration needs to be adapted depending on the $MgCl_2$ concentration present in the respective Reaction Mix)
LightCycler® Uracil DNA Glycosylase: 1 unit/reaction
LightCyler® 480 Probes Master
LightCycler® FastStart DNA Master HybProbe
LightCycler® Fast Start DNA Master PLUS HybProbe
PCR Protocol:

| | temp (° C.) | hold | ramp rate | acquisition |
|---|---|---|---|---|
| denaturation (1 cycle): | 95 | 10 min | 20 | none |
| amplification (45 cycles): | 95 | 10 sec | 20 | none |
| | 52-55 | 10 sec | 20 | single |
| | 72 | 12-22 sec | 20 | none |
| melting curve (1 cycle): | 95 | 0 sec | 20 | none |
| | 54 | 20 sec | 20 | none |
| | 45 | 20 sec | 0.2 | none |
| | 80 | 0 sec | 0.1 | cont. |
| cooling (1 cycle): | 40 | 30 sec | 20 | none |

TABLE 2

Primers and Probe used in FIGS. 3-5 for SCCmec RE2, RE3 and RE7 detection

| Name | Function | Label | Sequence | (SEQ ID NO:) |
|---|---|---|---|---|
| AR mec 12 fwd | RE2 detection | | 5'- TGA AAT GAA AGA CTG CGG AG -3' | (12) |
| AR mecA 3/13 | RE3 detection | | 5'- CCA CAT CTC ATT AAA TTT TTA AAT TAT ACA C -3' | (28) |
| AR mec 5/16 | RE7 detection | | 5'- CAA TCC TTT TTA TAT TTA AAA TAT ATT ATA CAC -3' | (32) |
| JU1 rev: | Specificity for SA | | 5'- CAA GGA AAG ATG CTA TCT TCC G -3' | (40) |
| AR mec Fluo 4-GV: | Specificity for MRSA | Flous | 5'- AAG TCG CTT TGC CCT TGG G -3' | (51) |
| AR mec 610 4-MM2-GV: | Specificity for MRSA | LC-Red 610 | 5'- CAT GCG TTG GTT CGA TTC TTG -3' | (76) |
| MRSA IC 4 | Internal Control | LC-Red 670 | 5'- CCA GCA GAA TGC AAA CCA -3' | (91) |

Reagent Concentrations Used in the Experiments Shown in FIGS. 3-5:
AR mec 12 fwd: 0.5 µM
AR meca 3/13: 0.3 µM
AR mec 5/16: 0.3 µM
JU1 rev: 0.5 µM
AR mec Fluo 4-GV: 0.2 µM
AR mec 610 4-MM2-GV: 0.2 µM
LightCycler® Uracil DNA Glycosylase: 1 unit/reaction
LightCyler® 480 Probes Master (final concentration in the PCR reaction is 3.2 mM $MgCl_2$.)
PCR Protocol Used in the Experiments Shown in FIGS. 3-5:

| | temperature | hold | ramp rate | acquisition |
|---|---|---|---|---|
| denaturation (1 cycle): | 95° C. | 10 min | 20 | none |
| amplification (45 cycles): | 95° C. | 10 sec | 20 | none |
| | 52° C. | 10 sec | 20 | single |
| | 72° C. | 18 sec | 20 | none |
| melting curve (1 cycle): | 95° C. | 0 sec | 20 | none |
| | 54° C. | 20 sec | 20 | none |
| | 45° C. | 20 sec | 0.2 | none |
| | 80° C. | 0 sec | 0.1 | cont. |
| cooling (1 cycle): | 40° C. | 30 sec | 20 | none |

A further Example was performed as described above with the exception that the following primers and probes were used:
AR mec 11 fwd: for RE2 detection
AR mecA 3/8: for RE3 detection AR mec 5/2: for RE7 detection
AR mec 6-2 rev: Specificity for SA
AR mec Fluo 4: Specificity for MRSA
AR mec 610 4-MM2: Specificity for MRSA In this example, curves similar to those shown in FIGS. 3 to 5 were obtained and Tm values of 57.21° C., 56.71° C. and 56.89° C. were calculated for RE2, RE3 and RE7, respectively.

Example 4

Analysis of a Preferred LC MRSA Assay System

A PCR assay for methicillin-resistant *Staphylococcus aureus* (MRSA) present on nasal swab specimens was developed with primers for amplification and FRET hybridization probes for detection of the amplified target nucleic acid with the LightCycler instrument. The assay was performed as described in the above Examples 1 to 3 unless otherwise noted.

This example describes the performance evaluation of a set of primers and probes (Roche LC MRSA assay system (PCR)).

| Oligo name | Label | Sequence (5'-3') | SEQ ID NO: |
|---|---|---|---|
| Primer, MRSA direct RE2 fwd | None | TGA AAT GAA AGA CTG CGG AG | 92 |
| Primer, MRSA direct RE3 fwd | None | CCA CAT CTC ATT AAA TTT TTA AAT TAT ACA C | 93 |
| Primer, MRSA direct RE7 fwd | None | CAA TCC TTT TTA TAT TTA AAA TAT ATT ATA CAC | 94 |
| Primer, MRSA direct rev | None | CAA GGA AAG ATG CTA TCT TCC G | 95 |
| Probe, MRSA direct Fluos | 3' Fluorescein | AAG TCG CTT TGC CCT TGG G | 96 |
| Probe, MRSA direct Red 610 | 5' LC Red 610, 3' Phosphat | CAT GCG TTG GTT CGA TTC TTG | 97 |
| Probe, MRSA direct IC Red 670 | 5' LC Red 670, 3' Phosphat | CCA GCA GAA TGC CAG CCA AT | 98 |

Workflow:

Nasal swabs delivered to the laboratory were broken off into a screw capped lysis tube containing 600 µl of neutralization buffer and approximately 50 µl of 0.1 mm glass beads. The tube was capped, heated for 2 minutes in a heating block set at 95 to 100° C. and processed on a MagNA Lyser for 70 seconds at a speed setting of 5000. The tube was centrifuged at 20,000×g for 1 minute and 5 µl of the liquid above the swab was used for PCR of MRSA.

PCR:

Three types of MRSA (RE2, RE3 and RE7) were detected with the PCR assay. Melting curve analysis of the 640 nm signal was used to detect MRSA. All three types of MRSA provided the same melting curve melting temperature. Melting curves above baseline with a $T_m$ within +/−2° C. of the positive control were considered positive. An internal control (IC) template was included in the assay using hybridization probe detection at 710 nm. Detection of the positive control in negative specimens was necessary to demonstrate lack of PCR inhibition.

Specificity

Coagulase negative *Staphylococcus* may have a portion of the PCR target. To confirm that isolates of these bacteria do not cross-react in the PCR, DNA from lysed cultures of 29 mecA-negative and 75 mecA-positive coagulase-negative staphylococci were tested. None of the coagulase-negative Staphylococci gave a positive result.

One hundred clinical isolates of *S. aureus* which are sensitive to methicillin (MSSA) were tested with PCR to determine if they give a false positive result with PCR. None of the *S. aureus* isolates gave a positive PCR result.

Inclusivity

DNA from lysed colonies of MRSA isolates from the US (207) and South Africa (105) were tested by PCR. Four MRSA isolates (1.3%) were not detected by PCR. Five MRSA isolates were detected with reduced sensitivity.

Exogenous Interference

PCR inhibition was tested by adding various amounts of whole blood to a swab and processing the sample according to the workflow description above. Spiking with 5 or 10 µl of whole blood showed no inhibition of the internal control. Adding 20 µl of blood gave less than 10% inhibition from replicate tests. Adding 70 µl of whole blood to the swab produced inhibition of PCR of the internal control with most replicate tests.

Sensitivity

The sensitivity of the PCR for the RE2, RE3 and RE7 MRSA targets was evaluated by testing in replicates of 5 the number of positive PCR results for dilutions of DNA from each MRSA type.

| | MRSA type | | |
|---|---|---|---|
| DNA copies | RE2 | RE3 | RE7 |
| 20 | 5 | 5 | 5 |
| 10 | 5 | 4 | 5 |
| 5 | 3 | 4 | 3 |
| 2.5 | 0 | 1 | 1 |

The sensitivity was ≧90% for all three MRSA types when 10 copies of DNA were used for PCR.

Clinical Sensitivity and Specificity

A clinical trial with 165 nasal swab specimens was performed. The gold standard for comparison was the culture-based detection method using CHROMagar MRSA (BD, Becton, Dickinson and Company, NJ, USA). Three swabs were found to be inhibitory to PCR. The following results were found with the remaining 162 swabs.

|  | | CHROMagar MRSA | |
|---|---|---|---|
|  | | Pos | Neg |
| MRSA PCR | Pos | 33 | 10* |
|  | Neg | 1 | 118 |

*5 of these 10 patients were on antibiotic treatment at the time of testing. Therefore, the data was recalculated based on whether or not the patients were on antibiotics.

|  | All patients | Patients not on antibiotics# |
|---|---|---|
| Sensitivity | 97.1% | 98.0% |
| Specificity | 92.2% | 95.2% |
| PPV | 76.7% | 90.9% |
| NPV | 99.2% | 99.0% |

These results indicate that excluding patients that were not on antibiotics may give a false negative result to the culture-based CHROMagar MRSA.

Swab Types

Three swab types were evaluated for use with MRSA PCR: Copan liquid Stuarts, Copan Amies Gel and Copan Amies Gel with charcoal swabs. All three swab types were found to give equivalent results regarding sensitivity and PCR inhibition.

What is claimed is:

1. A method of detecting the presence or absence of methicillin-resistant S. aureus (MRSA) in a sample, the method comprising performing an amplifying step comprising contacting the sample with a set of MRSA primers to produce an amplification product if MRSA is present in the sample, performing a hybridizing step comprising contacting the amplification product of step (a) with a pair of MRSA probes, wherein a first MRSA probe of the pair of MRSA probes is labeled with a donor fluorescent moiety and wherein a second MRSA probe of the pair of MRSA probes is labeled with a corresponding acceptor fluorescent moiety; and detecting the presence or absence of fluorescence resonance energy transfer (FRET) between the donor fluorescent moiety of the first MRSA probe and the acceptor fluorescent moiety of the second MRSA probe, wherein the presence of FRET is indicative of the presence of MRSA in the sample and wherein the absence of FRET is indicative of the absence of MRSA in the sample, wherein the method is capable of detecting each of Staphylococcal Chromosomal Cassettes (SCCmec) types I to V of MRSA, and wherein the set of primers comprises a primer set specific for MRSA type RE2, wherein the primer set comprises a primer that consists of the sequence 5'-TGA AAT GAA AGA CTG CGG AG-3' (MRSA direct RE2 fwd; SEQ ID NO:92);

a primer set specific for MRSA type RE3, wherein the primer set comprises a primer that consists of the sequence 5'-CCA CAT CTC ATT AAA TTT TTA AAT TAT ACA C-3' (MRSA direct RE3 fwd; SEQ ID NO:93), and a primer set specific for MRSA type RE7, wherein the primer set comprises a primer that consists of the sequence 5'-CAA TCC TTT TTA TAT TTA AAA TAT ATT ATA CAC-3' (MRSA direct RE7 fwd; SEQ ID NO:94).

2. The method of claim 1, wherein said primer specific for MRSA type RE2 is SEQ ID NO:92, wherein said primer specific for MRSA type RE3 is SEQ ID NO:93; and wherein said primer specific for MRSA type RE7 is SEQ ID NO:94.

3. The method of claim 1, wherein the set of primers additionally comprises a further primer specific for methicillin-resistant S. aureus (MRSA) as well as methicillin-sensitive S. aureus (MSSA).

4. The method of claim 3, wherein said further primer consists of the sequence

5'-CAA GGA AAG ATG CTA TCT TCC G-3' (MRSA direct rev; SEQ ID NO:95).

5. The method of claim 1, wherein the primer set consists of 5 primers.

6. The method of claim 1, wherein the primer set consists of 4 primers.

7. The method of claim 1, wherein the primer set consists of 3 primers.

8. The method of claim 1, wherein the set of primer comprises

MRSA direct RE2 fwd (SEQ ID NO:92), MRSA direct RE3 fwd (SEQ ID NO:93), MRSA direct RE7 fwd (SEQ ID NO:94) and, optionally a reverse primer.

9. The method of claim 8, wherein said reverse primer is R MRSA direct rev (SEQ ID NO:95).

10. The method of claim 1, wherein at least one probe of the pair of probes comprises a fluorescent moiety, wherein said at least one probe is selected from the group consisting of

```
                                  (AR mec Fluo 1; SEQ ID NO: 45)
5'- AAG TCG CTT TGC CTT TGG GTC A -3', (AR mec Fluo 2; SEQ ID NO: 46)
5'- TAC AAA GTC GCT TTG CCT TTG GGT CA -3', (AR mec Fluo 3; SEQ ID NO: 47)
5'- GGC CGT TTG ATC CGC CAA T -3', (AR mec Fluo 4; SEQ ID NO: 48)
5'- AAG TCG CTT TGC CCT TGG GTA -3', (AR mec Fluo 4-2; SEQ ID NO: 49)
5'- AAG TCG CTT TGC CCT TGG GT -3', (AR mec Fluo 4-3; SEQ ID NO: 50)
5'- AAG TCG CTT TGC CCT TGG GTC A -3', (AR mec Fluo 4-GV; SEQ ID NO: 51)
5'- AAG TCG CTT TGC CCT TGG G -3', (AR mec Fluo 4k; SEQ ID NO: 52)
5'- CAA GAA TTG AAC CAA CGC AT -3', (AR mec Fluo 5; SEQ ID NO: 53)
5'- CAA TGA CGA ATA CAT AGT CGC TTT GCC CTT -3', (AR mec Fluo 6; SEQ ID NO: 54)
5'- CGT TTG ATC CGC CAA TGA CGA -3', (AR mec Fluo 7; SEQ ID NO: 55)
5'- GCC AAT CCT TCG GAA GAT AGC A -3', (AR mec Fluo UR; SEQ ID NO: 56)
5'- ATT AAC ACA ACC CGC ATC -3', JU1 probe 1; SEQ ID NO: 57)
5'- GTC GCT TTG CCC TTG GGT C -3', JU2 probe 1; SEQ ID NO: 58)
5'- TCG CTT TGC CCT TGG GTC AT -3', JU3 probe 1; SEQ ID NO: 59)
5'- GGC CGT TTG ATC CGC CAA T -3', JU4 probe1; SEQ ID NO: 60)
5'- GTC CTT GTG CAG GCC GTT TGA T -3', JU5 probe1; SEQ ID NO: 61)
5'- CTT GGG TCA TGC GTT GGT TCA ATT -3', (AR mec 640 3; SEQ ID NO: 62)
5'- CGA ATA CAA AGT CGC TTT GCC CTT GGG -3', (AR mec 640 4; SEQ ID NO: 63)
5'- ATG CGT TGG TTC AAT TCT TG -3', (AR mec 610 4-3; SEQ ID NO: 64)
5'- GCG TTG GTT CAA TTC TTG GG -3', (AR mec 640 4k; SEQ ID NO: 65)
5'- ACC CAA GGG CAA AGC GAC TT -3', (AR mec 640 5; SEQ ID NO: 66)
5'- GGT AAT GCG TTG GTT CAA TTC TTG -3', (AR mec 640 6; SEQ ID NO: 67)
5'- ACA AAG TCG CTA TGC CCT TGG GTC A -3', (AR mec 640 7; SEQ ID NO: 68)
5'- CTT TCC TTG TAT TTC TAA TGT AAT GAC TG -3', (AR mec 640 UR; SEQ ID NO: 69)
5'- TTG ATG TGG GAA TGT CAT TTT GCT GAA -3', JU1 probe 2; SEQ ID NO: 70)
5'- GCG TTG GTT CAA TTC TTG GGC CAA T -3', JU2 probe 2; SEQ ID NO: 71)
5'- GTT GGT TCA ATT CTT GGG CCA ATC CTT CG -3', JU3 probe 2; SEQ ID NO: 72)
5'- CGA ATA CAA AGT CGC TTT GCC CTT GG -3', JU4 probe2; SEQ ID NO: 73)
5'- GCC AAT GAC GAA TAC AAA GTC GCT TTG CC -3', JU5 probe2; SEQ ID NO: 74)
5'- TGG GCC AAT CCT TCG GAA GAT AGC A -3', (AR mec 610 4-MM2; SEQ ID NO: 75)
5'- ATG CGT TGG TTC GAT TCT TG -3', (AR mec 610 4-MM2-GV; SEQ ID NO: 76)
5'- CAT GCG TTG GTT CGA TTC TTG -3', (MRSA direct Fluos; SEQ ID NO: 96)
5'- AAG TCG CTT TGC CCT TGG G -3',
and
                                    (MRSA direct Red 610; SEQ ID NO: 97)
5'- CAT GCG TTG GTT CGA TTC TTG -3'.
```

11. The method of claim 10, wherein
the first probe including the first label is fluorescein-5'-AAG TCG CTT TGC CCT TGG GTA-3' (AR mec Fluo 4; SEQ ID NO:48) and the second probe including the second label is LC-Red 610-5'-ATG CGT TGG TTC GAT TCT TG-3' (AR mec 610 4-MM2; SEQ ID NO:75),
the first probe including the first label is fluorescein-5'-AAG TCG CTT TGC CCT TGG G-3' (AR mec Fluo 4-GV; SEQ ID NO:51) and the second probe including the second label is LC-Red 610-5'-CAT GCG TTG GTT CGA TTC TTG-3' (AR mec 610 4-MM2-GV; SEQ ID NO:76), or
the first probe including the first label is 5'-AAG TCG CTT TGC CCT TGG G-3'-fluorescein (MRSA direct Fluos; SEQ ID NO:96) and the second probe including the second label is LC-Red 610-5'-CAT GCG TTG GTT CGA TTC TTG-3' (MRSA direct Red 610; SEQ ID NO:97).

12. The method of claim 10, wherein the probe comprises a fluorescent moiety and a functionally active variant of any of the probes of SEQ ID NO:45, 51, 75, 76, 96 or 97, wherein
(a) the functionally active variant is a functionally active part of a probe of SEQ ID NO:45, 51, 75, 76, 96 or 97, the part encompassing at least 70% of any of the sequences of SEQ ID NO:45, 51, 75, 76, 96 or 97;
(b) the functionally active variant is a functionally active variant having at least 85% sequence identity with any of the sequences of SEQ ID NO:45, 51, 75, 76, 96 or 97;
(c) the functionally active variant is a probe of SEQ ID NO:45, 51, 75, 76, 96 or 97 comprising at least one chemically modified nucleic acid; and/or
(d) the functionally active variant is a functionally active variant complementary to any of the sequences of SEQ ID NO:45, 51, 75, 76, 96 or 97 or complementary to any of the functionally active variants of (a), (b) and/or (c).

13. The method of claim 1, wherein
the first probe is 5'-AAG TCG CTT TGC CCT TGG GTA-3' (AR mec Fluo 4; SEQ ID NO:48) and the second probe is 5'-ATG CGT TGG TTC GAT TCT TG-3' (AR mec 610 4-MM2; SEQ ID NO:75),
the first probe is fluorescein-5'-AAG TCG CTT TGC CCT TGG G-3' (AR mec Fluo 4-GV; SEQ ID NO:51) and the second probe including the second label is LC-Red 610-

5'-CAT GCG TTG GTT CGA TTC TTG-3' (AR mec 610 4-MM2-GV; SEQ ID NO:76), or the set of primer comprises MRSA direct RE2 fwd (SEQ ID NO:92), MRSA direct RE3 fwd (SEQ ID NO:93), MRSA direct RE7 fwd (SEQ ID NO:94) and, optionally, MRSA direct rev (SEQ ID NO:95), and wherein the first probe is 5'-AAG TCG CTT TCG CCT TGG G-3' (MRSA direct Fluos; SEQ ID NO:96) and wherein the second probe is 5'-CAT GCG TTG GTT CGA TTC TTG-3' (MRSA direct Red 610; SEQ ID NO:97).

14. The method of claim 1, wherein the members of the pair of MRSA probes hybridize to the amplification product within no more than five nucleotides of each other.

15. The method of claim 1, wherein the members of the pair of MRSA probes hybridize to the amplification product within no more than four nucleotides of each other.

16. The method of claim 1, wherein the members of the pair of MRSA probes hybridize to the amplification product within no more than three nucleotides of each other.

17. The method of claim 1, wherein the members of the pair of MRSA probes hybridize to the amplification product within no more than two nucleotides of each other.

18. The method of claim 1, wherein the members of the pair of MRSA probes hybridize to the amplification product within no more than one nucleotide of each other.

19. The method of claim 1, wherein the donor fluorescent moiety is fluorescein; and/or wherein the acceptor fluorescent moiety is selected from the group consisting of LC-Red 610, LC-Red 640, LC-Red 670, LC-Red 705, Cy5, and Cy5.5.

20. A method of detecting the presence or absence of methicillin-resistant S. aureus (MRSA) in a sample, the method comprising performing an amplifying step comprising contacting the sample with a set of MRSA primers to produce an amplification product if MRSA is present in the sample, performing a hybridizing step comprising contacting the amplification product of step (a) with a MRSA probe, wherein the MRSA probe is labeled with a donor fluorescent moiety and with a corresponding acceptor fluorescent moiety; and detecting the presence or absence of fluorescence resonance energy transfer (FRET) between the donor fluorescent moiety and the acceptor fluorescent moiety of the MRSA probe, wherein the presence or absence of FRET is indicative of the presence or absence of MRSA in the sample, wherein the method is capable of detecting each of Staphylococcal Chromosomal Cassettes (SCCmec) types I to V of MRSA, wherein the set of primers comprises a primer set specific for MRSA type RE2, wherein the primer set comprises a primer that consists of the sequence shown in SEQ ID NO: 92, a primer set specific for MRSA type RE3, wherein the primer set comprises a primer that consists of the sequence shown in SEQ ID NO:93, and a primer set specific for MRSA type RE7, wherein the rimer set comprises a primer that consists of the sequence shown in SEQ ID NO:94.

21. The method of claim 20, wherein the set of primers comprises one or more of the primers selected from the group consisting of SEQ ID NO: 92, 93 and 94;

wherein the probe comprises two fluorescent moieties and is selected from the group consisting of SEQ ID NO:45, 51, 75, 76, 96 and 97;

wherein the amplifying step employs a polymerase enzyme having 5' to 3' exonuclease activity;

wherein the donor and acceptor fluorescent moieties are within no more than 5 nucleotides of each other on the probe;

wherein the probe comprises a nucleic acid sequence that permits secondary structure formation, wherein the secondary structure formation results in spatial proximity between the donor and acceptor fluorescent moiety; and/or wherein the acceptor fluorescent moiety is a quencher.

22. The method of claim 1 or 20, wherein the detecting step comprises exciting the sample at a wavelength absorbed by the donor fluorescent moiety and visualizing and/or measuring the wavelength emitted by the acceptor fluorescent moiety.

23. The method of claim 22, wherein the detecting comprises quantitating the FRET.

24. The method of claim 1 or 20, wherein the presence of the FRET within 55 cycles is indicative of the presence of MRSA in the sample.

25. The method of claim 24, wherein the presence of the FRET within 45 cycles is indicative of the presence of MRSA in the sample.

26. The method of claim 24, wherein the presence of the FRET within 35 cycles is indicative of the presence of MRSA in the sample.

27. The method of claim 1 or 20, wherein the detecting step is performed after each amplification and hybridization step and/or in real-time.

28. The method of claim 1 or 20, further comprising determining the melting temperature between one or both of the probe(s) and the amplification product of step (a), wherein the melting temperature confirms the presence or the absence of MRSA.

29. The method of claim 1 or 20, further comprising:

preventing amplification of a contaminant nucleic acid, wherein preventing comprises performing the amplification step (a) in the presence of uracil and treating the sample with uracil-DNA glycosylase prior to a first amplifying step.

30. The method of claim 1 or 20, wherein the method is performed on a control sample.

31. The method of claim 30, wherein the control sample comprises a MRSA nucleic acid molecule.

32. The method of claim 1 or 20, wherein the sample is a biological sample.

33. The method of claim 32, wherein said biological sample is selected from the group consisting of a swab of an infected wound, a skin swab, a nasal swab, a throat swab, a groin swab, an axilla swab, a swab from a site of an invasive device, a swab from a site of possible infection, a body fluid, a blood sample, a urine sample and a perineum swab.

34. A kit comprising:

a set of primers comprising a primer set specific for MRSA type RE2, wherein the primer set comprises a primer that consists of the sequence shown in SEQ ID NO: 92, a primer set specific for MRSA type RE3, wherein the primer set comprises a primer that consists of the sequence shown in SEQ ID NO:93, and a primer set specific for MRSA type RE7, wherein the primer set comprises a primer that consists of the sequence shown in SEQ ID NO:94;

a pair of probes selected from the group consisting of SEQ ID NO:45, 51, 75, 76, 96 and 97; and a donor fluorescent moiety and a corresponding fluorescent moiety labeling the probe(s), wherein the primers and probes in said kit are capable of detecting each of Staphylococcal Chromosomal Cassettes (SCCmec) types I to V of MRSA.

35. The kit of claim 34, further comprising a package label or package insert having instructions thereon for using the set of MRSA primers and the pair of MRSA probes to detect the presence or absence of MRSA in a sample.

36. The kit of claim 34, further comprising at least one suitable enzyme and/or a suitable buffer.

37. The kit of claim 36, wherein said enzyme is uracil-DNA glycosylase or a DNA polymerase.

* * * * *

UNITED STATES PATENT AND TRADEMARK OFFICE
CERTIFICATE OF CORRECTION

PATENT NO. : 8,535,888 B2  
APPLICATION NO. : 11/966287  
DATED : September 17, 2013  
INVENTOR(S) : Christian Aichinger Page 1 of 1

It is certified that error appears in the above-identified patent and that said Letters Patent is hereby corrected as shown below:

In the Claims

Column 76, line 66 (Claim 9), please delete "is R" and insert --is--, therefor.

Column 77, line 1 - Column 78, line 24 (Claim 10), please delete the entire claim and insert the following therefor:
--The method of claim 1, wherein at least one probe of the pair of probes comprises a fluorescent moiety, wherein said at least one probe is selected from the group consisting of
5'- AAG TCG CTT TGC CCT TGG GTA -3' (AR mec Fluo 4; SEQ ID NO: 48),
5'- AAG TCG CTT TGC CCT TGG G -3' (AR mec Fluo 4-GV; SEQ ID NO: 51),
5'- ATG CGT TGG TTC GAT TCT TG -3' (AR mec 610 4-MM2; SEQ ID NO: 75),
5'- CAT GCG TTG GTT CGA TTC TTG -3' (AR mec 610 4-MM2-GV; SEQ ID NO: 76),
5'-AAG TCG CTT TGC CCT TGG G-3' (MRSA direct Fluos; SEQ ID NO: 96), and
5'-CAT GCG TTG GTT CGA TTC TTG-3' (MRSA direct Red 610; SEQ ID NO: 97).   --.

Column 79, line 57 (Claim 20), please delete "rimer" and insert --primer--, therefor.

Signed and Sealed this  
Twenty-ninth Day of April, 2014

Michelle K. Lee  
*Deputy Director of the United States Patent and Trademark Office*